(12) United States Patent
Suzuki et al.

(10) Patent No.: US 12,102,311 B2
(45) Date of Patent: Oct. 1, 2024

(54) ORGAN RETRACTION DEVICE

(71) Applicant: TERUMO KABUSHIKI KAISHA, Tokyo (JP)

(72) Inventors: Miria Suzuki, Kanagawa (JP); Katsumi Morimoto, Kanagawa (JP); Yoshihito Machida, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 254 days.

(21) Appl. No.: 17/737,192

(22) Filed: May 5, 2022

(65) Prior Publication Data

US 2022/0257229 A1     Aug. 18, 2022

Related U.S. Application Data

(63) Continuation of application No. PCT/JP2020/025581, filed on Jun. 29, 2020.

(30) Foreign Application Priority Data

Nov. 5, 2019  (JP) .................................. 2019-200945

(51) Int. Cl.
*A61B 17/02* (2006.01)
*A61B 17/00* (2006.01)

(52) U.S. Cl.
CPC ...... *A61B 17/0218* (2013.01); *A61B 17/0281* (2013.01); *A61B 2017/00004* (2013.01); *A61B 2017/00876* (2013.01); *A61B 2017/0225* (2013.01)

(58) Field of Classification Search
CPC ............ A61B 17/0218; A61B 17/0281; A61B 2017/0225

USPC .......................................................... 600/208
See application file for complete search history.

(56) References Cited

U.S. PATENT DOCUMENTS

| 6,080,168 A | 6/2000 | Levin et al. |
| 8,870,882 B2 * | 10/2014 | Kleiner .............. A61B 17/1671 606/86 A |
| 9,918,708 B2 | 3/2018 | Livne et al. |
| 2011/0071361 A1 | 3/2011 | Mollenauer et al. |
| 2014/0031630 A1 * | 1/2014 | Nguyen ................. A61B 17/02 600/204 |

(Continued)

FOREIGN PATENT DOCUMENTS

| JP | H06-508049 A | 9/1994 |
| WO | WO 92/21291 A2 | 12/1992 |

OTHER PUBLICATIONS

International Search Report for International Application No. PCT/JP2020/025581, mailed Aug. 18, 2020.

(Continued)

*Primary Examiner* — Eduardo C Robert
*Assistant Examiner* — Christina Negrellirodriguez
(74) *Attorney, Agent, or Firm* — Sheridan Ross P.C.

(57) ABSTRACT

An organ retraction device includes a surgical instrument and an expandable body operable for expansion by connection of the surgical instrument thereto. The expandable body includes a first expandable section configured to be expandable to a predetermined size and shape in a first stage to move an organ in an abdominal cavity, and a second expandable section configured to be expandable to a predetermined size and shape in a second stage to fix the organ.

18 Claims, 20 Drawing Sheets

(56) References Cited

U.S. PATENT DOCUMENTS

2014/0275795 A1\* 9/2014 Little ................. A61B 17/3423
600/208
2016/0007981 A1\* 1/2016 Govindarajan ........ A61B 17/02
600/208

OTHER PUBLICATIONS

International Preliminary Report on Patentability for International Application No. PCT/JP2020/025581, mailed May 19, 2022.

\* cited by examiner

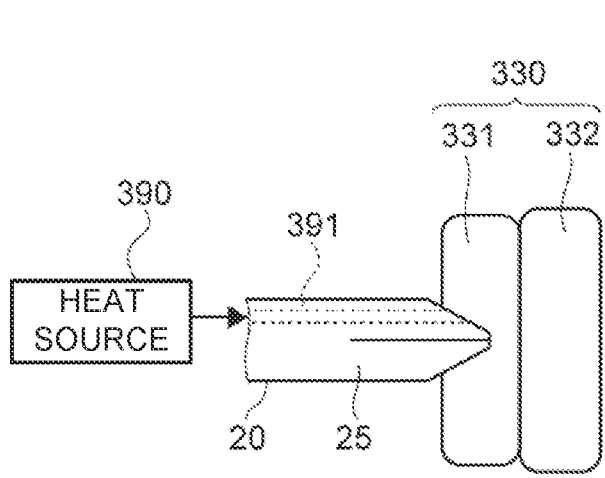
FIG. 6A
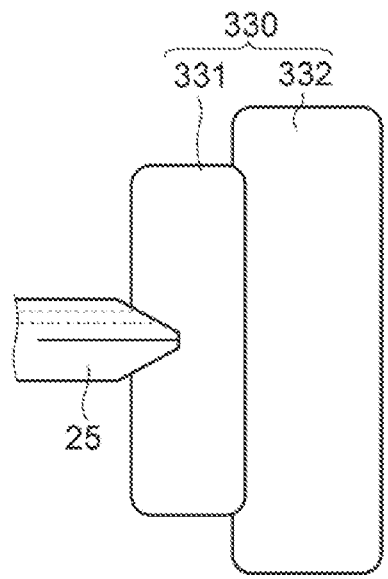
FIG. 6B
FIG. 6C
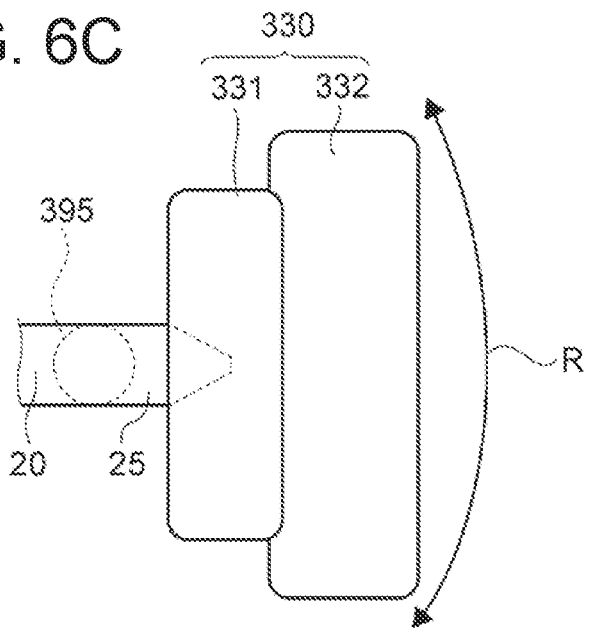
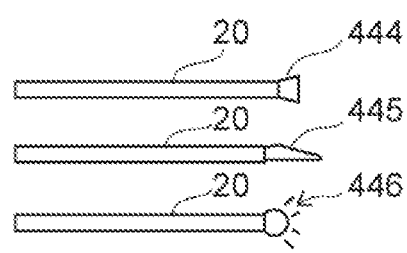
FIG. 6D
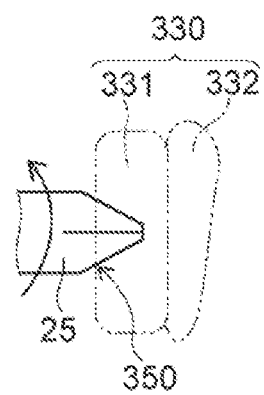
FIG. 6E FIG. 11A
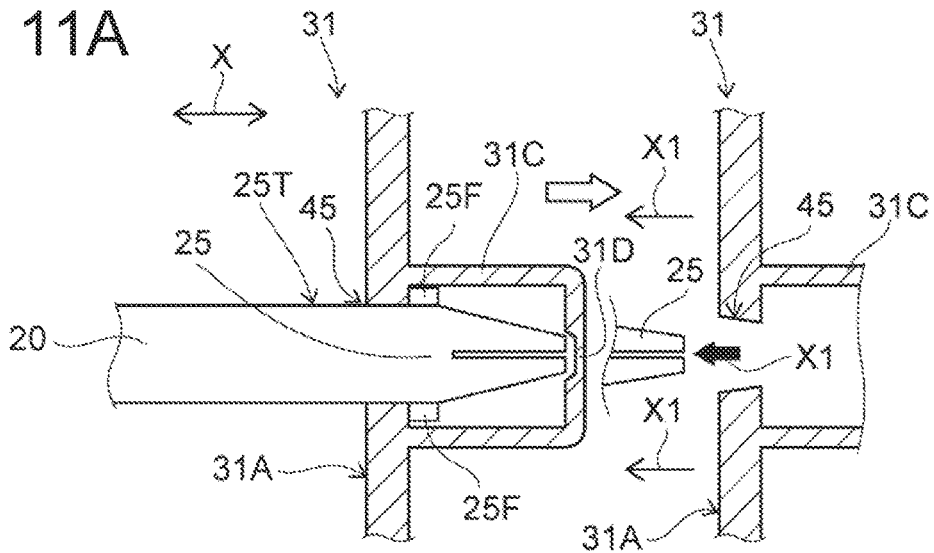
FIG. 11B
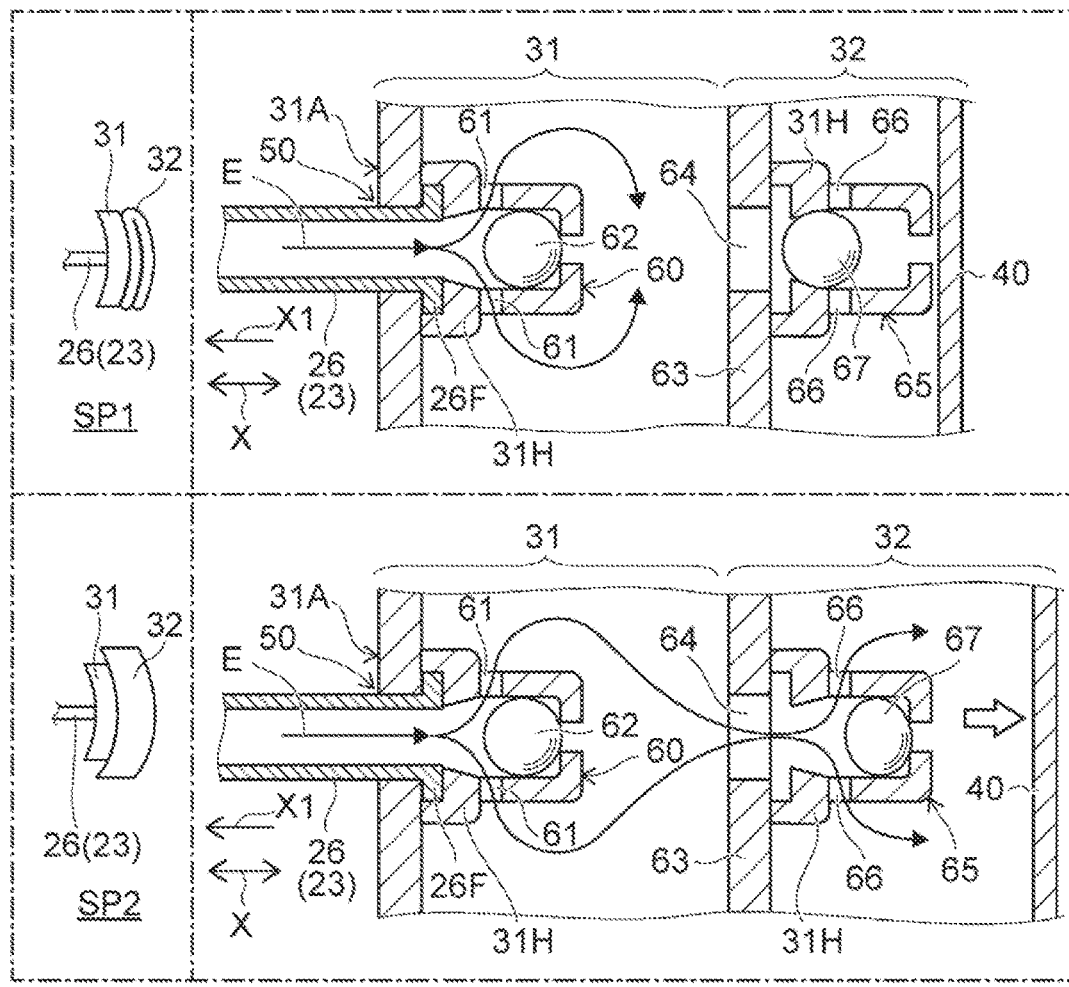
FIG. 11C FIG. 20A
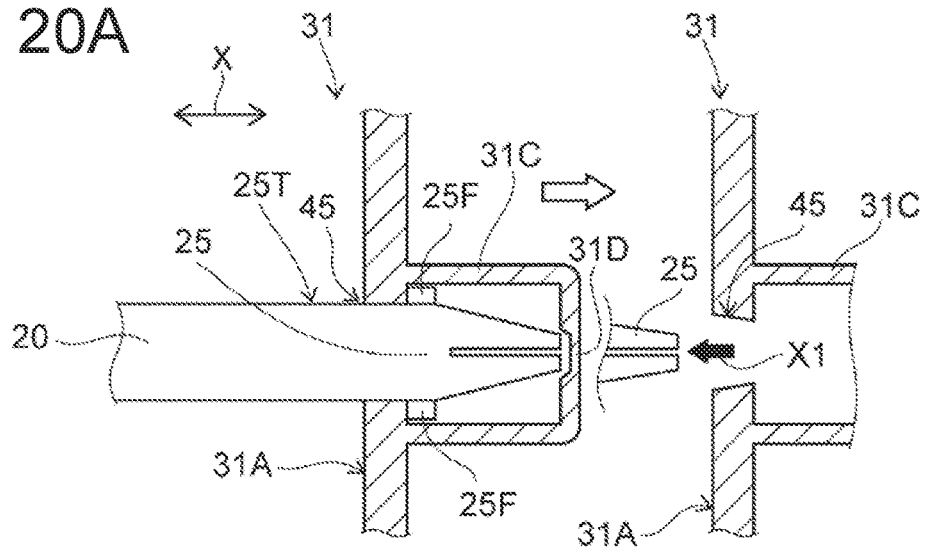
FIG. 20B
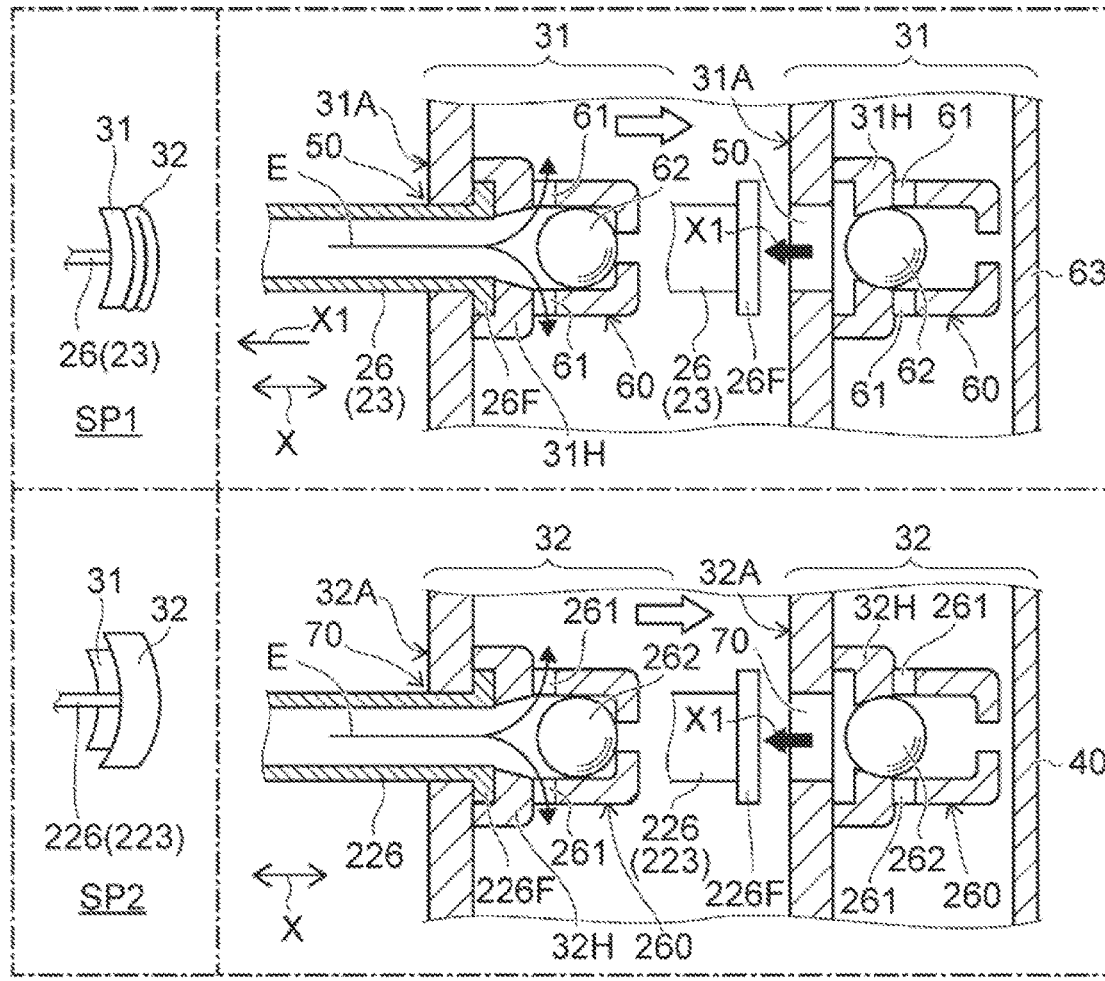
FIG. 20C

ORGAN RETRACTION DEVICE

CROSS-REFERENCE TO RELATED APPLICATIONS

The present application is a continuation of and claims benefit to PCT Application No. PCT/JP2020/025581 filed on Jun. 29, 2020, entitled "ORGAN EXCLUSION TOOL" which claims priority to Japanese Patent Application No. 2019-200945 filed on Nov. 5, 2019. The entire disclosures of the applications listed above are hereby incorporated herein by reference, in their entirety, for all that they teach and for all purposes.

BACKGROUND

The present disclosure relates to an organ retraction device that performs, for example, retraction of an organ in the abdominal cavity.

A laparoscopic surgery is used as a low-invasive treatment that substitutes for an open abdominal surgery on the digestive system and the like, and has found increasing applications. A laparoscopic surgery is minimally invasive, but is performed using a camera of, for example, approximately 1 cm in diameter. A limitation is hence imposed on a range of visual field available for a healthcare practitioner during a laparoscopic surgery.

To secure a range of visual field, for example, in a surgery for bowel cancer, another organ that lies over the large intestine, more specifically the small intestine or the like is grasped and pushed aside or retracted by a pair of forceps to keep the large intestine exposed as a target organ for the surgery. There is also a need to fix the retracted small intestine or the like to avoid its dislocation in the abdominal cavity. Such pushing aside of an organ and fixation of the retracted organ is called "retraction" in combination.

Operative techniques for this retraction are applied to a patient held in a head-down posture. The term "head-down posture" means that the body of a patient is held tilted on a surgery bed with the head of the patient positioned lower than the body. The retracted organ such as the retracted small intestine is fixed by inserting surgical gauze or the like into the body.

The above-mentioned method of organ retraction in a head-down posture however involves problems to be described hereinafter. Head-down tilt is accompanied by an elevation in intraocular pressure, and therefore has a risk of development of a visual field deficit, well-leg compartment syndrome, or deep vein thrombosis (DVT). The fixing force by gauze is weak, and the retracted organ is dislocated under motor activities, so that this organ comes into a field of vision. It is accordingly difficult to perform a long-term surgery, to say nothing of ensuring safety during such a surgery. There is also a danger of hurting the organ because the organ is grasped and pushed aside by a pair of forceps.

U.S. Pat. No. 9,918,708 describes to hook over and push aside an organ by using a device instead of gauze. In U.S. Pat. No. 9,918,708, a tissue retractor head and a handle are disclosed, and the tissue retractor head is attached to the handle. When the tissue retractor head is filled with a fluid and is expanded from a collapsed state, the tissue retractor head can hook over a tissue in the abdominal cavity. In the collapsed state, the tissue retractor head is inserted into the abdominal cavity through a laparoscopic port.

BRIEF SUMMARY

As will be described next, however, problems arise if an attempt is made to perform pushing aside or retraction of an organ and fixation of the organ in the abdominal cavity by using the tissue retractor head disclosed in U.S. Pat. No. 9,918,708. If the tissue retractor head has a large size, the tissue retractor head cannot move with ease in the abdominal cavity and is hard to perform pushing aside or retraction of an organ with precision, for example, when performing pushing aside of retraction of the small intestine or the like that lies over the large intestine. If the tissue retractor head has a small size, on the other hand, it can perform pushing aside or retraction of the organ, but is hard to fix the retracted small intestine or the like over a wide area due to its insufficient size.

It is with respect to the above issues and other problems that the embodiments presented herein were contemplated. Among other things, the present disclosure provides an organ retraction device that allows to secure a field of vision for a surgery and to safely and reliably perform a surgery by pushing aside or retracting another organ, which lies over a target organ for the surgery, and performing fixation of the retracted other organ to keep the target organ exposed for the surgery.

In an aspect of the present disclosure, the above-described problems can be solved by an organ retraction device including a surgical instrument, and an expandable body operable for expansion by connection of the surgical instrument thereto. The expandable body includes a first expandable section configured to be expandable to a predetermined size and shape in a first stage to move an organ in the abdominal cavity, and a second expandable section configured to be expandable to a predetermined size and shape in a second stage to fix the organ.

According to the configuration described above, the first expandable section and second expandable section of the expandable body are expanded in the different stages by the surgical instrument. It is therefore possible to secure a field of vision for a surgery and to safely and reliably perform the surgery by pushing aside or retracting the other organ, which lies over the target organ for the surgery, with the first expandable section and performing fixation of the retracted other organ with the second expandable section to keep the target organ exposed for the surgery.

Preferably, the surgical instrument may include a pair of forceps having a grasp portion, and may deliver a fluid with the grasp portion connected to the expandable body so that the first expandable section and the second expandable section are expanded in the abdominal cavity, and the grasp portion may be configured to be capable of grasping when the surgical instrument is detached from the expandable body.

According to this configuration, the first expandable section and the second expandable section can be expanded by delivering a fluid from the grasp portion of the pair of forceps to the expandable body. When the grasp portion is detached from the expandable body, the grasp portion of the pair of forceps can perform grasping operation as a function of the pair of forceps. The pair of forceps can therefore be used according to the procedure or operative technique for the surgery.

In some examples, the first expandable section and the second expandable section may have collapsed conformations, respectively, before expansion.

According to this configuration, the first expandable section and the second expandable section are collapsed and therefore can be inserted with ease into the abdominal cavity.

In some examples, the expandable body may be sealed so that a fluid supplied from a side of the surgical instrument, to which the expandable body is connected, into the expandable body is prevented from leaking out of the expandable body.

According to this configuration, the expandable body can be expanded from a collapsed state by filling it with a fluid, and the fluid does not leak from the expandable body in an expanded state. The expandable body can therefore maintain the expanded state.

In some examples, the expandable body may be made of a pliable material.

According to this configuration, the expandable body can be stretched and easily expanded from a collapsed state.

In some examples, the expandable body may have a hand shape.

According to this configuration, the expandable body can be hooked over the organ such as the small intestine so that the organ can be stably pushed aside or fixed.

In some examples, the expandable body may have a C shape.

According to this configuration, a pressure produced between the expandable body and the organ can be dispersed, leading to an increase in an overall fixing force to the organ.

In some examples, the expandable body may have a wavy surface.

According to this configuration, an increased friction force can be provided between the expandable body and the organ, leading to an increase in an overall fixing force to the organ.

In some examples, the expandable body may include a magnet and may be fixable to the surgical instrument by the magnet.

According to this configuration, the expanded expandable body can be firmly fixed with the magnet in the abdominal cavity.

In some examples, the expandable body may have a valve structure configured to suppress leakage of a fluid in the expandable body to an outside of the expandable body when the surgical instrument is detached from the expandable body.

According to this configuration, even after the surgical instrument is detached from the expandable body, the fluid in the expandable body does not leak so that the expandable body can remain in the expanded state in the abdominal cavity.

In some examples, the expandable body may be configured such that, after expansion, the resulting expanded expandable body contracts when the surgical instrument detached from the expandable body is inserted into the valve structure.

According to this configuration, when the expandable body is taken out of the abdominal body after completion of the surgery, the expanded expandable body can be caused to contract, thereby facilitating recovery of the expandable body from the interior of the abdominal cavity. Application of operative techniques can be simplified accordingly.

In some examples, the surgical instrument may be configured to be connected to the expandable body when pierced into the valve structure.

According to this configuration, when the expandable body is taken out of the abdominal body after completion of the surgery, the expanded expandable body can be caused to contract by cutting the expandable body with the forceps, thereby facilitating recovery of the expandable body from the interior of the abdominal cavity. Application of operative techniques can be simplified accordingly.

In some examples, the surgical instrument may be configured to be connected to the expandable body when rotated relative to the valve structure.

According to this configuration, the surgical instrument can be connected to the valve structure by rotating it like a key, and therefore the reliability of the connection of the surgical instrument to the expandable body is increased.

In some examples, the expandable body may be configured to contract when, after expansion, the surgical instrument detached from the expandable body cuts the expandable body.

According to this configuration, when the expandable body is taken out of the abdominal body after completion of the surgery, the expanded expandable body can contract if cut by the surgical instrument, thereby facilitating the recovery of the expandable body from the interior of the abdominal cavity. Application of operative techniques can be simplified accordingly.

In some examples, the expandable body may be made of a bioabsorbable material.

According to this configuration, the expandable body can be left over or placed after completion of the surgery, thereby obviating the recovery of the expandable body from the interior of the abdominal cavity. Application of operative techniques can be simplified accordingly.

In some examples, the expandable body may have a size selected according to a size of the abdominal cavity.

According to this configuration, one of expandable bodies of different sizes can be selected and used according to the size of the abdominal cavity of each individual patient. The reliability of application of operative techniques may be increased accordingly.

In some examples, the expandable body may be produced by a 3D printer.

According to this configuration, bespoke production of the expandable body is enabled using the 3D printer, for example, on the basis of test results of computerized tomography (CT) or the like. The reliability of application of operative techniques may be increased accordingly.

In some examples, a material having radiopacity may be used in the expandable body.

According to this configuration, even if a part of the expandable body is torn off, irradiation of an X-ray makes it possible to find through images that the torn part of the expandable body remains in the abdominal cavity.

In some examples, the surgical instrument may include an electric scalpel, and the expandable body may have an insulating coating so that expandable body does not puncture even if the electric scalpel comes into contact with the expandable body.

According to this configuration, an incident can be prevented even if an electric scalpel is used during application of the operative technique.

In some examples, a water-absorbing material may be used in a part of the expandable body, where the expandable body comes into contact with an abdominal wall.

According to this configuration, it is possible to ensure enhancement of a friction force for the fixation of the expandable body in the abdominal cavity and a dry environment in the abdominal cavity.

Among other things, the organ retraction device according to the present disclosure allows to secure a field of vision for a surgery and to safely and reliably perform the surgery by pushing aside or retracting another organ, which lies over a target organ for the surgery, and performing fixation of the retracted other organ to keep the target organ exposed for the surgery.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages are described herein and will be apparent to those skilled in the art upon consideration of the following Detailed Description and in view of the figures.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIGS. 6A to 6E are views illustrating various modifications of some elements in the organ retraction device in accordance with examples of the present disclosure;

FIG. 11A is a schematic diagram illustrating a structure example of a connection port in the organ retraction device illustrated in FIG. 8;

FIGS. 11B and 11C are schematic diagrams illustrating a fluid injection port in first and second stages respectively of expansion of the expandable body in the organ retraction device illustrated in FIG. 8;

FIG. 20A is a schematic diagram illustrating a structural example of a connection port of the organ retraction device illustrated in FIG. 16;

FIG. 20B is a schematic diagram illustrating a structural example of a fluid injection port of a first expandable section of the organ retraction device illustrated in FIG. 16;

FIG. 20C is a schematic diagram illustrating a structural example of a fluid injection port of a second expandable section of the organ retraction device illustrated in FIG. 16;

DETAILED DESCRIPTION

Figure 1:
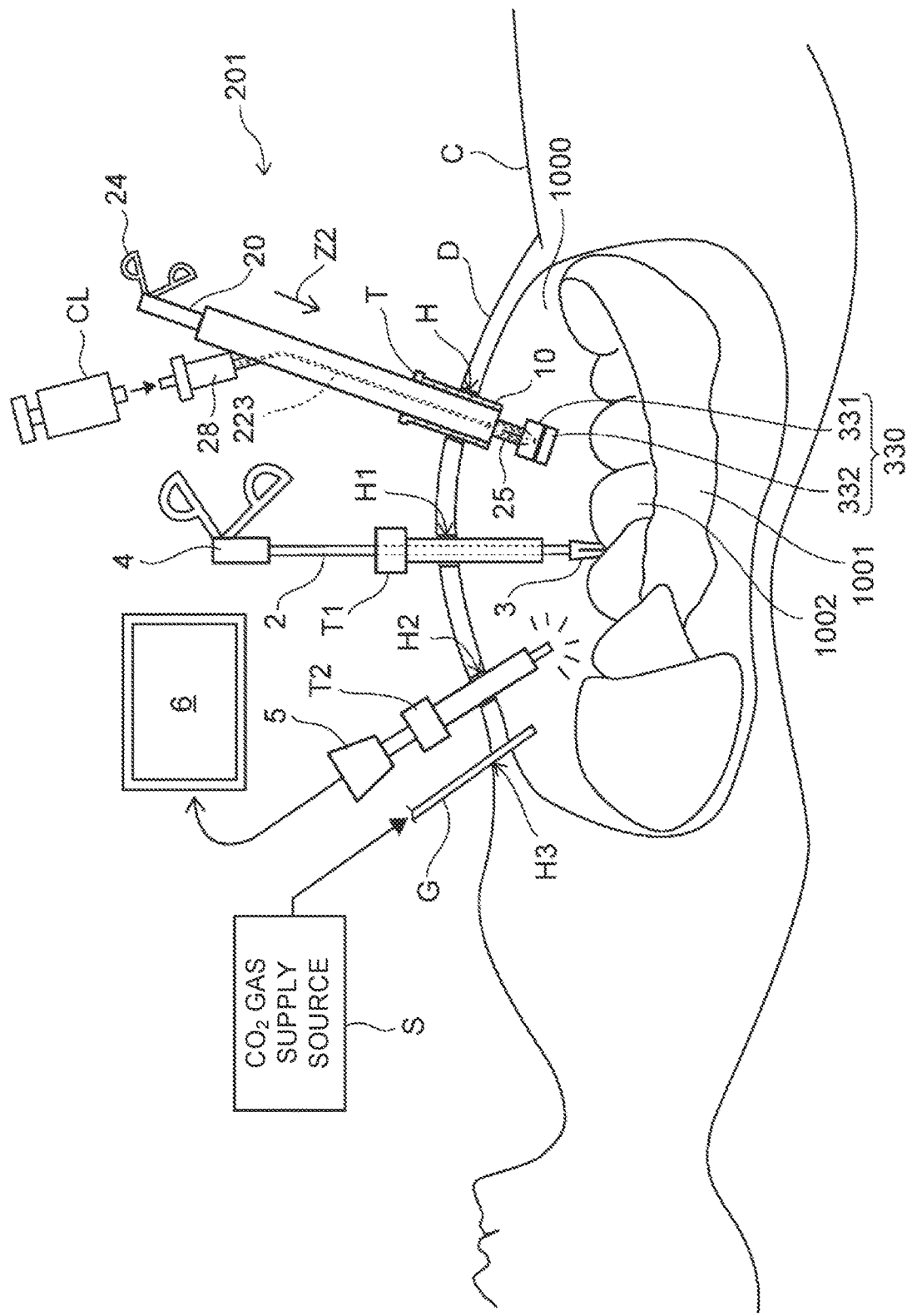
FIG. 1 is a schematic diagram illustrating a first example of an organ retraction device used in a laparoscopic surgery in accordance with examples of the present disclosure.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The ensuing description provides embodiments only, and is not intended to limit the scope, applicability, or configuration of the claims. Rather, the ensuing description will provide those skilled in the art with an enabling description for implementing the described embodiments. It being understood that various changes may be made in the function and arrangement of elements without departing from the spirit and scope of the appended claims. In the individual figures, like elements are identified by like reference numerals, and their detailed descriptions are omitted as appropriate.

Various aspects of the present disclosure will be described herein with reference to drawings that may be schematic illustrations of idealized configurations.

Figure 2:
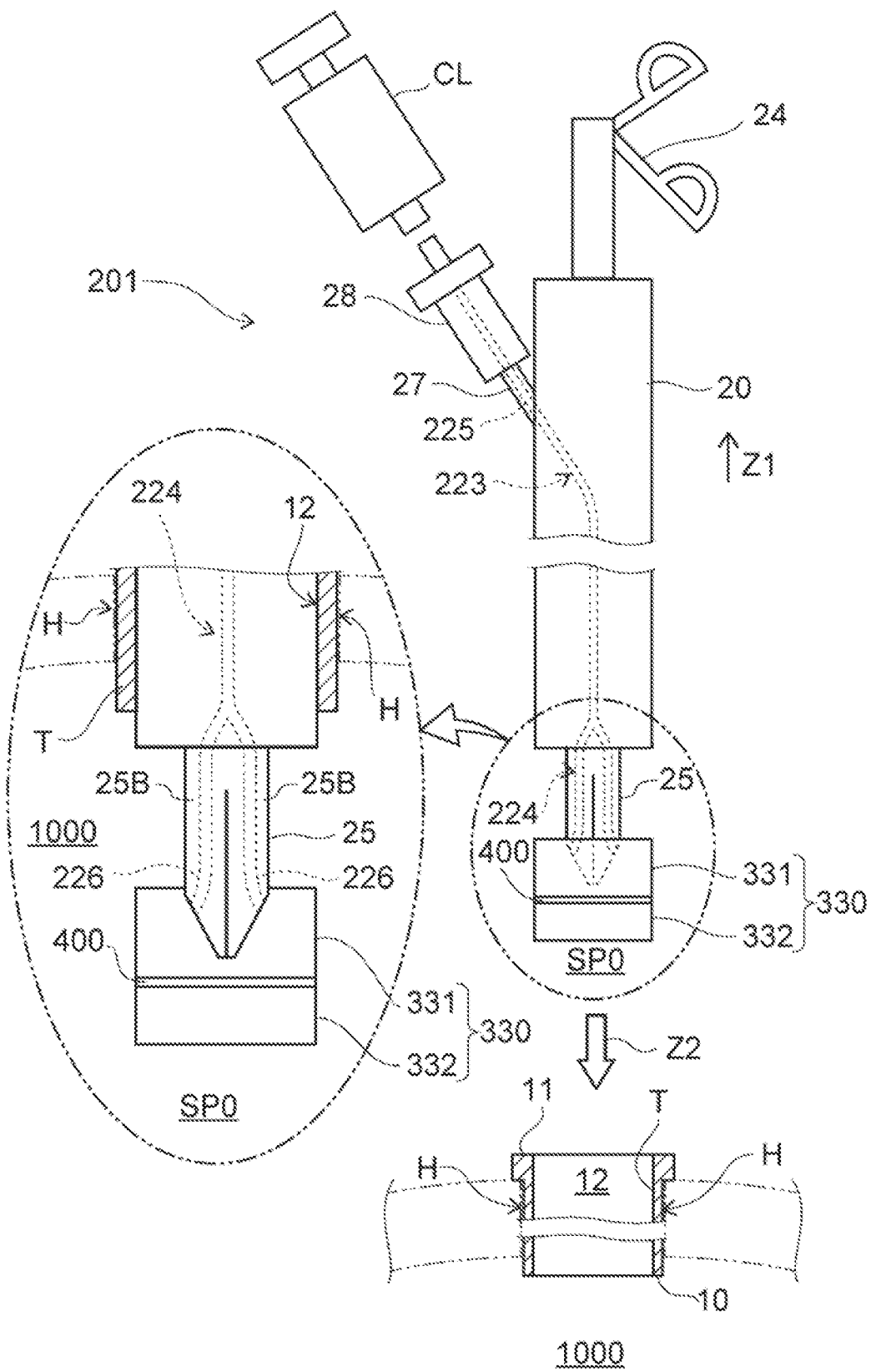
FIG. 2 is a partial cross-sectional front view illustrating a configuration example of the organ retraction device illustrated in FIG. 1.

FIG. 1 is a schematic diagram illustrating a first example of an organ retraction device 201 used in a laparoscopic surgery in accordance with examples of the present disclosure. FIG. 2 is a partial cross-sectional front view illustrating a configuration example of the organ retraction device 201 illustrated in FIG. 1.

The organ retraction device 201 illustrated in FIG. 1 is used, for example, in laparoscopic surgery. A laparoscopic surgery has found utility as a minimally invasive surgery as a substitute for an open abdominal surgery on the digestive system and the like. A laparoscopic surgery is minimally invasive, but is performed using a laparoscopic camera of, for example, approximately 1 cm in diameter.

A description will be made of an example in which a surgery, for example, for bowel cancer is performed using the laparoscopic surgery. With a range of visual field secured in the laparoscopic surgery, another organ that lies over a target organ for a surgery, for example, the small intestine or the like that lies over the large intestine in a surgery for bowel cancer is pushed aside or retracted to keep the large intestine exposed as the target organ for the surgery. For this purpose, the retracted small intestine or the like is fixed to avoid its dislocation in the abdominal cavity during the surgery. Such pushing aside of an organ other than a target organ for a surgery and fixation of the retracted organ is called "retraction" in combination.

In the laparoscopic surgery using the organ retraction device 201, it is possible to reduce the time or tilt, during which a patient is held head-down for applying operative techniques for the retraction of the other organ with the organ retraction device 201. The laparoscopic surgery using the organ retraction device 201 also leads to fewer occasions where the retracted small intestine or the like is fixed by inserting surgical gauze into the body, thereby reducing or completely avoiding the possibility of missing surgical gauze left in the body after surgery.

In the laparoscopic surgery illustrated in FIG. 1, one or more, for example, a plurality of skin incision sites (which may be referred to herein as "incision sites" or "ports," etc.) H, H1, H2, and H3 are opened in the abdomen D of a patient C. A trocar tube T may be inserted into the incision site H, another trocar tube T1 into the incision site H1, and a further trocar tube T2 into the incision site H2. Further, a gas supply tube G may be inserted into the incision site H3. The gas supply tube G supplies carbon dioxide ($CO_2$) gas from a $CO_2$ gas supply source S into the abdominal cavity 1000, whereby the abdominal cavity 1000 is inflated.

The trocar tubes T, T1, and T2 may be referred to herein as "trocars." Each of the trocar tubes T, T1, and T2 is a hollow metal body, has rigidity, and enables to extractably introduce various instruments into the abdominal cavity 1000. As described above, the incision sites H to H3 are opened as a part of the laparoscopic surgery. For the patient, however, surgical incisions are small, pain is mild, damage to internal organs are small, and post-surgery recovery is fast, all, compared with a conventional open abdominal surgery.

As illustrated in FIG. 1, a pair of forceps 2 (hereinafter referred to as "the additional forceps 2") is extractably inserted in the trocar tube T1. The additional forceps 2 have a grasp portion 3 at a distal end portion (e.g., inner end portion) on a side of one end thereof, and a hand control part 4 on a side of the other end (e.g., external end portion) thereof. The grasp portion 3 may be positioned in the abdominal cavity 1000. A laparoscopic camera 5 may be extractably inserted in the trocar tube T2. The laparoscopic camera 5 captures color images of conditions in the abdominal cavity 1000 while lighting the interior of the abdominal cavity 1000. Healthcare practitioners proceed with the surgery while monitoring the scene of the surgery on a monitor screen 6 (e.g., based on the images captured by the laparoscopic camera 5 and rendered by the monitor screen 6, etc.).

With reference to FIGS. 1 and 2, a description will next be made about the organ retraction device 201. As illustrated in FIG. 1, the organ retraction device 201 is extractably inserted into the trocar tube T. The organ retraction device 201 pushes aside or retracts the other organ that lies over the target organ for the surgery, for example, the large intestine 1001 in a surgery for bowel cancer, for example, the small intestine 1002 or the like to keep the large intestine 1001 exposed as the target organ for the surgery. The organ retraction device 201 then fixes the retracted other organ, for example, the small intestine 1002 or the like to avoid dislocation, or movement, of the other organ in the abdominal cavity 1000 (e.g., during surgery, etc.).

In FIG. 2, the organ retraction device 201, the above-mentioned trocar tube T, and the incision site H are illustrated. The trocar tube T is extractably inserted into the incision site H. One end portion (e.g., inner end portion) of the trocar tube T serves as a distal end opening 10, while the other end portion (e.g., outer end portion) of the trocar tube T serves as an insertion opening 11. The distal end opening 10 and the insertion opening 11 are communicated to each other via an insertion passage 12. The distal end opening 10 is placed in the abdominal cavity 1000. The organ retraction device 201 illustrated in FIG. 2 includes a pair of forceps 20 (hereinafter referred to as "the forceps 20") and an expandable body 330. The forceps 20 are an example of a surgical instrument for performing insertion of the expandable body 330, expansion operation of the expandable body 330, placement of the expandable body 330 in the abdominal cavity 1000, and the like as will be described subsequently herein.

The forceps 20 have a hand control part 24 and a grasp portion 25. The grasp portion 25 is disposed at the one end portion (e.g., inner end portion) of the forceps 20, while the hand control part 24 is disposed at the other end portion (e.g., outer end portion) of the forceps 20. The grasp portion 25 can be operated to open or close by manipulation of the hand control part 24 (e.g., lever, etc.). When a healthcare practitioner manipulates the hand control part 24, the grasp portion 25 is operated open or closed. In the state illustrated in FIG. 2, the expandable body 330 is grasped by the grasp portion 25, and the grasp portion 25 is detachably, liquid-tightly, and/or gas-tightly connected to the expandable body 330. The expandable body 330 is in a collapsed state. The insertion passage 12 of the trocar tube T has an inner diameter of a size large enough to permit insertion of the forceps 20 and the collapsed expandable body 330 therethrough.

The forceps 20 are configured such that, by inserting them in a direction Z2 into the insertion passage 12 of the trocar tube T, the grasp portion 25 and the expandable body 330, which is grasped in the collapsed state by the grasp portion 25, can be inserted into the abdominal cavity 1000 through the insertion passage 12. After the surgery, on the other hand, the grasp portion 25 and the expandable body 330, which is grasped by the grasp portion 25, and has been caused to contract to a small size by release of a fluid, can be pulled out of the abdominal cavity 1000 by pulling the forceps 20 out in a direction Z1 through the insertion passage 12.

As illustrated in FIG. 2, the forceps 20 also have a connector portion 28, and a fluid flow conduit 223 for allowing a fluid to flow therethrough. The connector portion 28 is connected to a fluid supplier CL such as a syringe. One end portion 224 of the fluid flow conduit 223 is disposed in the grasp portion 25, and a large majority of the fluid flow conduit 223 extends through the forceps 20. The other end portion 225 of the fluid flow conduit 223 extends to the connector portion 28. The fluid flow conduit 223 may be a conduit, for example, of a circular cross-section formed in the forceps 20, or may be disposed by arranging, for example, a plastic-made flexible tubular member in the forceps 20. The one end portion 224 of the fluid flow conduit 223 is disposed extending to a distal end portion of the grasp portion 25. The one end portion 224 of the fluid flow conduit 223 has branch conduits 226 arranged, for example, in a bifurcated manner. Distal end openings of these branch conduits 226 communicate outwardly on sides of distal ends of associated forceps members 25B of the grasp portion 25 as indicated by broken lines.

The fluid supplier CL can therefore supply the fluid to a predetermined pressure or predetermined amount in a first expandable section 331 of the collapsed expandable body 330 through the fluid flow conduit 223 and the distal end openings of the branch conduits 226 of the grasp portion 25. Accordingly, the fluid expands the collapsed expandable body 330, so that the expandable body 330 is allowed to hold an expanded state. Examples of the fluid which the fluid supplier CL supplies may include, but are in no way limited to, gases such as carbon dioxide and air, and liquids such as physiological saline. Additionally or alternatively, the fluid may also be one formed by mixing a liquid such as physiological saline in a gas. Such mixing of a liquid in a gas can enhance the ability to expand the expandable body 330. If a carbon dioxide gas is used, it may be configured to supply the carbon dioxide gas from the carbon dioxide gas supply source S to the fluid supplier CL.

Referring to FIGS. 2 to 4C, the expandable body 330 will be described next.

Figure 3:
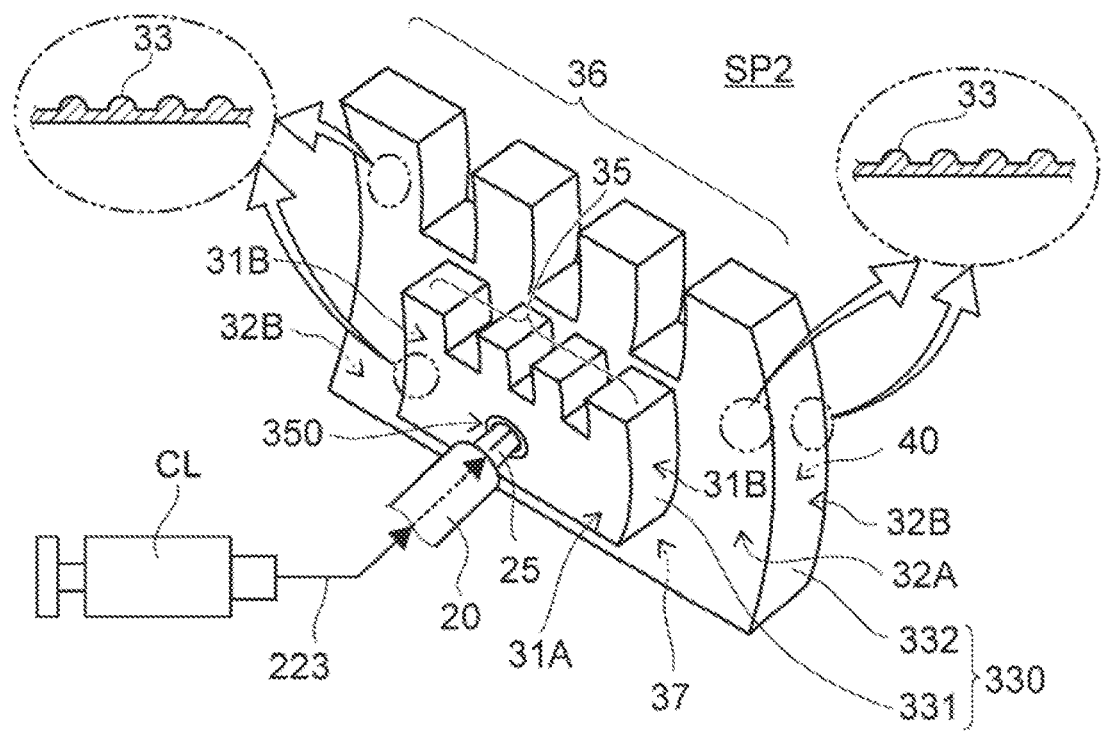
FIG. 3 is a schematic diagram illustrating an expandable body of the organ retraction device in a state where the expandable body is expanded to a predetermined size and shape in accordance with examples of the present disclosure.
Figures 4A, 4B, 4C:
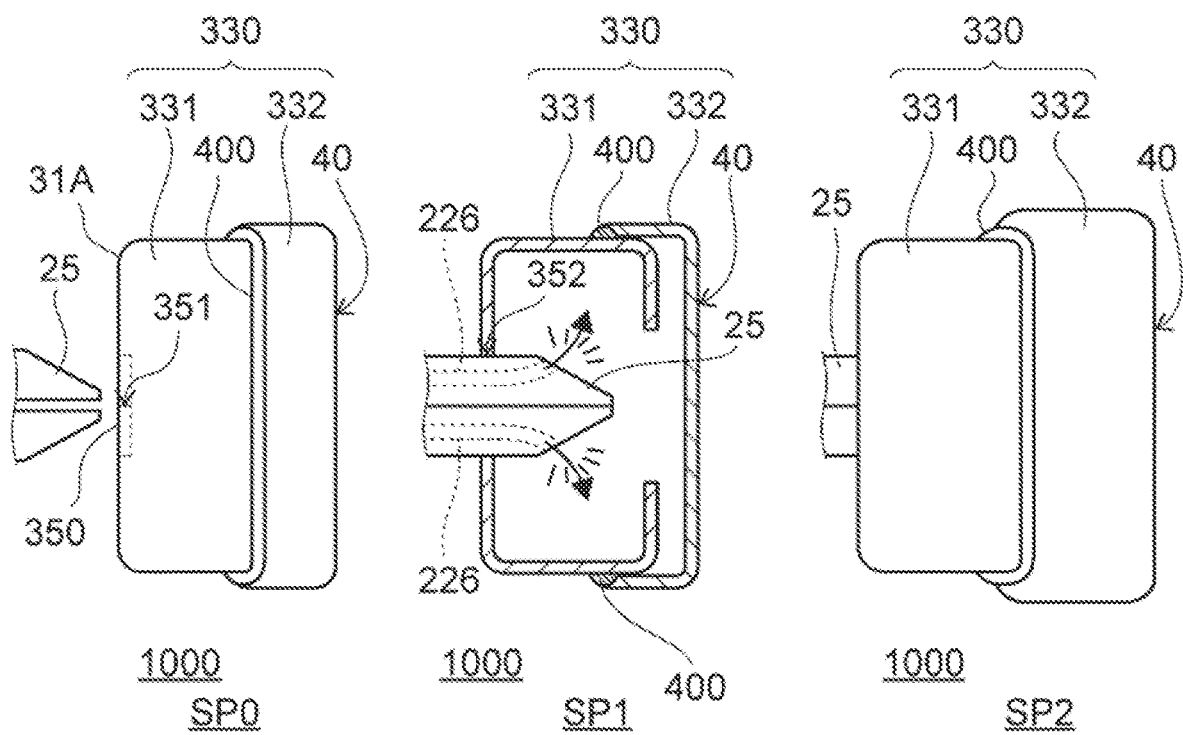
FIGS. 4A to 4C are views illustrating the expandable body expanding from a collapsed state to an expanded state as illustrated in FIG. 3.

FIG. 3 illustrates the expandable body 330 in a state where the expandable body is expanded to a predetermined size and shape, and FIGS. 4A to 4C illustrate the expandable body 330 expanding from the collapsed state to an expanded state as illustrated in FIG. 3. FIG. 4A is a schematic diagram of the first expandable section 331 and a second expandable section 332 of the expandable body 330 in collapsed states before injection of the fluid (e.g., this state may be referred to herein as the "preliminary stage SP0"). FIG. 4B is a schematic diagram of a state, in which only the first expandable section 331 is expanded to a predetermined size and shape by the injection of the fluid and the second expandable section 332 remains in the collapsed state (e.g., this state may be referred to herein as the "first stage SP1"). Further, FIG. 4C is a schematic diagram of the first expandable section 331 and the second expandable section 332 in states both expanded to predetermined sizes and shapes, respectively, by the injection of the fluid into the first expandable section 331 and the second expandable section 332 (e.g., this state may be referred to herein as the "second stage SP2").

The expandable body 330 illustrated in FIG. 3 comprises the first expandable section 331 and the second expandable section 332. The first expandable section 331 and the second expandable section 332 may form an integrated single bag body, and may be made of a material having pliability, for example, a thin plastic material or a thin rubber material. In some examples, the material may include, but is in no way limited to, a high molecular material such as silicone rubber, latex rubber, polyolefin, crosslinked polyolefin, polyvinyl chloride, polyamide, polyamide elastomer, polyester, polyester elastomer, polystyrene elastomer, polyurethane, polyurethane elastomer, fluorinated resin, polyimide, polycarbonate, alkylbenzenesulfonate (ABS), polytetrafluoroethylene, cellulose acetate, polyether sulfone, acrylic resin, or silicone resin, and/or a mixture thereof. Examples of the polyolefin may include resin materials such as polyethylene, polypropylene, polybutene, ethylene-propylene copolymer, ethylene-vinyl acetate copolymer, ionomer, and/or a mixture of two or more of them. Additionally or alternatively, it is also possible to use a metal material such as stainless steel, aluminum alloy, or superelastic metal. In some examples, the first expandable section 331 and the second expandable section 332 may be made of polyurethane, polyamide, epoxy resin, and/or the like.

Between the first expandable section 331 and the second expandable section 332, a weak portion 400 is disposed as illustrated in FIG. 2 and FIGS. 4A to 4C. The weak portion 400 may also be referred to herein as a "weak seal portion" or a "to-be-separated portion." The weak portion 400 may be formed over the entirety or a part of a periphery between the first expandable section 331 and the second expandable section 332. The weak portion 400 has such a function that, when a predetermined amount of the fluid is injected into the first expandable section 331, only the first expandable section 331 is operated to expand, but the second expandable section 332 is allowed to remain in the collapsed state without expansion. In one example, separation strength of the weak portion 400 by filling of the fluid under pressure upon injection of the fluid into the first expandable section 331 may be approximately 0.1 to 20 N/cm. If the expanding force by the filling of the fluid under pressure exceeds the separation strength of the weak portion 400, the weak portion 400 is broken so that the second expandable section 332 is separated and released from the first expandable section 331. The second expandable section 332 is therefore expanded to the predetermined size and shape. The weak portion 400 can be formed by adopting fusion bonding, for example, by thermal fusion bonding, high frequency bonding or ultrasonic bonding, or organic solvent bonding.

In the preliminary stage SP0 illustrated in FIGS. 2 and 4A, the first expandable section 331 and the second expandable section 332 are both in collapsed states. In the first stage SP1 illustrated in FIG. 4B, the first expandable section 331 of the expandable body 330 is expanded by the injection of the fluid, but the second expandable section 332 is not expanded yet. In the second stage SP2 illustrated in FIG. 4C, the first expandable section 331 and the second expandable section 332 are both expanded by the injection of the fluid.

More specifically, after beginning to inject the fluid into the collapsed first expandable section 331 in the preliminary stage SP0 illustrated in FIG. 4A, the fluid is injected to the predetermined pressure or predetermined amount in the first stage SP1 illustrated in FIG. 4B, whereby only the first expandable section 331 is expanded to the predetermined size and shape. However, the weak portion 400 remains in a state that it keeps the second expandable section 332, which is in the collapsed state, united with the expanded first expandable section 331. Therefore, the second expandable section 332 remains collapsed without expansion. When the fluid is further injected to the predetermined pressure or predetermined amount, the collapsed state of the second expandable section 332 can no longer be maintained by the weak portion 400 in the second stage SP2 illustrated in FIG. 4C, so that the second expandable section 332 is expanded to the predetermined size and shape while the expanded state of the first expandable section 331 is maintained.

As a device or means for injecting the fluid, the fluid supplier CL illustrated, for example, in FIGS. 1 and 3 may be used. As illustrated in FIG. 2, the fluid supplier CL is detachably connected to the connector portion 28. The fluid supplier CL is configured such that, when the healthcare practitioner depresses a push part (e.g., plunger, etc.) of the fluid supplier CL (e.g., syringe, etc.), a predetermined amount of the fluid in the fluid supplier CL is supplied to a side of the expandable body 330 through the connector portion 28 and the fluid flow conduit 223.

Taking a laparoscopic surgery for bowel cancer as an example, the first expandable section 331 plays a role to push aside or retract the other organ (e.g., the small intestine 1002, and/or the like) that lies over the target organ (e.g., the large intestine 1001) for the surgery as illustrated in FIG. 1, and to expose the target organ (e.g., the large intestine 1001) for the surgery. On the other hand, the second expandable section 332 plays a role to fix the retracted other organ, specifically, the small intestine 1002 or the like to avoid its dislocation in the abdominal cavity 1000. Therefore, the volume of the second expandable section 332 of the expandable body 330 in the state that the second expandable section 332 has been expanded is set greater than the volume of the first expandable section 331 in its expanded state to fix the retracted other organ without dislocation in the abdominal cavity 1000.

As illustrated in FIG. 3, the first expandable section 331 and the second expandable section 332 may be formed in a comb shape or hand shape in the states that, as illustrated in FIGS. 1 and 2, are expanded in a vicinity of the distal end opening 10 of the trocar tube T. The expandable body 330 can therefore be hooked over an organ such as the small intestine, thereby enabling to reliably push aside and fix the organ. Moreover, the first expandable section 331 can push aside or retract the small intestine or the like with an increased force, and the second expandable section 332 can fix the retracted small intestine or the like with an increased force. Even if the fluid is supplied in the same amount, compared with formation of the expandable sections in rectangular prismatic shapes, the first expandable section 331 can be ensured to have great external dimensions for use in the pushing aside or retracting work for the organ, and the second expandable section 332 can be ensured to have great external dimensions for use in the fixing work for the retracted organ. The first expandable section 331 and the second expandable section 332 may be formed, for example, of an elastically deformable, thin plastic film of vinylidene chloride resin, polyurethane, or the like, and/or a thin rubber film of latex or the like, so that the first expandable section 331 and the second expandable section 332 may easily expand when the fluid is injected and contract into the contracted states when the fluid is released conversely.

As illustrated in FIG. 3, the first expandable section 331 has an attachment surface 31A, left and right side surfaces 31B, an upper comb portion 35, and a bottom surface portion 37. Similarly, the second expandable section 332 has an inner surface portion 32A, left and right side surfaces 32B, an upper comb portion 36, a bottom surface portion 37, and a pressing surface portion 40. The first expandable section 331 and the second expandable section 332 each have a curved shape, for example, a C shape. The attachment surface 31A and the inner surface portion 32A are formed as concave surfaces. The pressing surface portion 40 is formed as a convex surface. The first expandable section 331 is curved, and therefore can push aside or retract the organ while pushing it up. The second expandable section 332 is also curved, and therefore can fix the retracted organ in the pushed-up state. It is therefore possible to secure a field of vision as needed during the surgery. Further, the expandable body 330 can be held in place such that it is tightly squeezed between the belly side and the back side, because the first expandable section 331 and second expandable section 332 of the expandable body 330 are each curved to have the C shape. The formation of the first expandable section 331 and the second expandable section 332 in these shapes can increase the overall fixing force. However, the shapes of the first expandable section 331 and the second expandable section 332 are merely illustrative, and other shapes can be adopted as desired. For example, the second expandable section 332 may be formed in a shape having no comb portion. In this case, the second expandable section 332 may be formed in such a shape that the retracted organ does not slip out even if it is small.

In the first stage SP1 of FIG. 4B, the first expandable section 331 is expanded in the vicinity of the distal end opening 10 of the trocar tube T as illustrated in FIGS. 1 and 2, but the second expandable section 332 is not expanded and is collapsed. In this state, the first expandable section 331 plays a role to push aside or retract the other organ (e.g., the small intestine 1002, and/or the like) that lies over the target organ (e.g., the large intestine 1001) for the surgery. As illustrated in FIG. 4C, the first expandable section 331 and the second expandable section 332 have been both expanded in the second stage SP2, so that the pressing surface portion 40 plays a role to fix the retracted other organ, for example, the small intestine 1002 or the like to avoid its dislocation in the abdominal cavity 1000.

As illustrated in FIGS. 3 and 4A, the first expandable section 331 has a seal structure portion 350 on a side of the attachment surface 31A. The seal structure portion 350 illustrated in FIG. 4A centrally has a thin valve structure 351. When the grasp portion 25 of the forceps 20 is pierced into the thin valve structure 351 of the seal structure portion 350, a hole 352 is opened in the seal structure portion 350 as illustrated in FIG. 4B. With the grasp portion 25 inserted in the hole 352, the forceps 20 detachably grasp the first expandable section 331. The forceps 20 are liquid-tightly and/or gas-tightly connected to the first expandable section 331 at the valve structure 351 of the seal structure portion 350. As it is only necessary to pierce the grasp portion 25 into the thin valve structure 351 of the seal structure portion 350, application of operative techniques can be simplified. The seal structure portion 350 is closed up by the grasp portion 25 of the forceps 20 as described above, so that the fluid injected into the first expandable section 331 does not leak from the seal structure portion 350. The fluid can therefore be injected without leakage into the first expandable section 331 through the fluid flow conduit 223 and the grasp portion 25.

The first expandable section 331 and the second expandable section 332 may have, at the surfaces thereof, fine wave-shaped or concavo-convex shaped portions 33 as illustrated in FIG. 3. These fine wave-shaped or concavo-convex shaped portions 33 further enhance the friction force to the organ. Accordingly, the expandable body 330 can push aside or retract an organ other than the large intestine 1001, for example, the small intestine 1002 or the like to have the large intestine 1001 exposed as the target organ for the surgery, and can also fix the retracted small intestine 1002 or the like to avoid its dislocation in the abdominal cavity 1000. Owing to the increased friction force with the small intestine 1002 or the like, the first expandable section 331 and the second expandable section 332 can therefore more reliably fix the retracted small intestine 1002 or the like to avoid its dislocation in the abdominal cavity 1000.

It is to be noted that the expanded first expandable section 331 and the second expandable section 332 can provide an increased fixing force by disposing a magnet at a portion of the expandable body 330, the portion being to be placed on a side of the abdominal wall, and attracting the magnet to a metal portion fixed outside the body. In this manner, the reliability of organ retraction can be improved.

Using an example in which the above-mentioned organ retraction device 201 is applied to a laparoscopic surgery for bowel cancer, a method of use of the organ retraction device 201 will be described next.

As illustrated in FIGS. 1 and 2, the expandable body 330 is collapsed small at the beginning, and is grasped by the grasp portion 25 of the forceps 20. As illustrated in FIG. 1, the forceps 20 and the expandable body 330 of the organ retraction device 201 are inserted into the abdominal cavity 1000 through the trocar tube T.

When a pushing-aside operation is performed with the expandable body 330 in retraction, an organ other than the large intestine 1001, for example, the small intestine 1002 or the like is pushed aside to have the large intestine 1001 exposed as the target organ for the surgery. Through the fluid flow conduit 223 and the branch conduits 226 of the grasp portion 25, the fluid supplier CL illustrated in FIG. 2 supplies the fluid to the predetermined pressure or predetermined amount in the first expandable section 331 of the expandable body 330 as illustrated in FIG. 4B. The first expandable section 331 of the expandable body 330 is therefore expanded from the collapsed state to the predetermined size and shape, and is maintained in the expanded state.

Figure 5A:
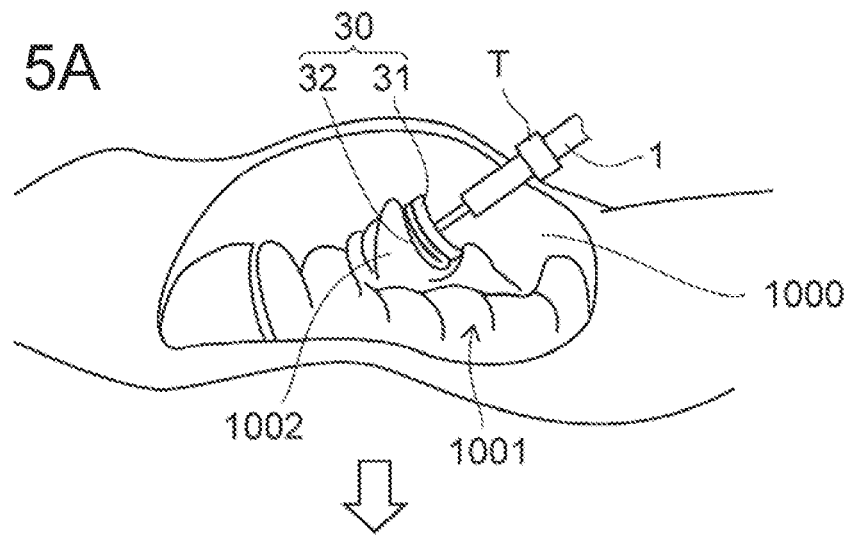
FIGS. 5A to 5C are views illustrating a pushing aside or retracting operation of an organ, a fixing operation of the organ, and a manner of detaching a pair of forceps from the expandable body when the expandable body is placed in the abdominal cavity, respectively, all, using the organ retraction device illustrated in FIG. 1.

As illustrated from FIG. 4A to FIG. 4B, the first expandable section 331 is expanded to a predetermined volume. FIG. 5A illustrates a state in which only the first expandable section 331 of the expandable body 330 is expanded to the predetermined size and shape. When the healthcare practitioner manipulates the hand control part 24 of FIG. 1, the first expandable section 331 pushes aside the small intestine 1002 or the like in the abdominal cavity 1000 as illustrated by way of example in FIG. 5A. The large intestine 1001 as the target organ for the surgery is therefore exposed in the field of vision.

The retracted small intestine 1002 or the like is next fixed to avoid its dislocation during the surgery. Here, the fluid supplier CL illustrated in FIG. 2 supplies the fluid into the first expandable section 331 of the expandable body 330 through the fluid flow conduit 223 and the branch conduits 226 of the grasp portion 25 until the first expandable section 331 is brought into the predetermined size and shape as illustrated in FIG. 4B. As illustrated in FIG. 4C, the weak portion 400 is therefore broken so that the second expandable section 332 is released from the first expandable section 331. Accordingly, the second expandable section 332 is expanded from the collapsed state to the predetermined size and shape so that the volume of the second expandable section 332 becomes great compared with that of the first expandable section 331.

Figure 5B:
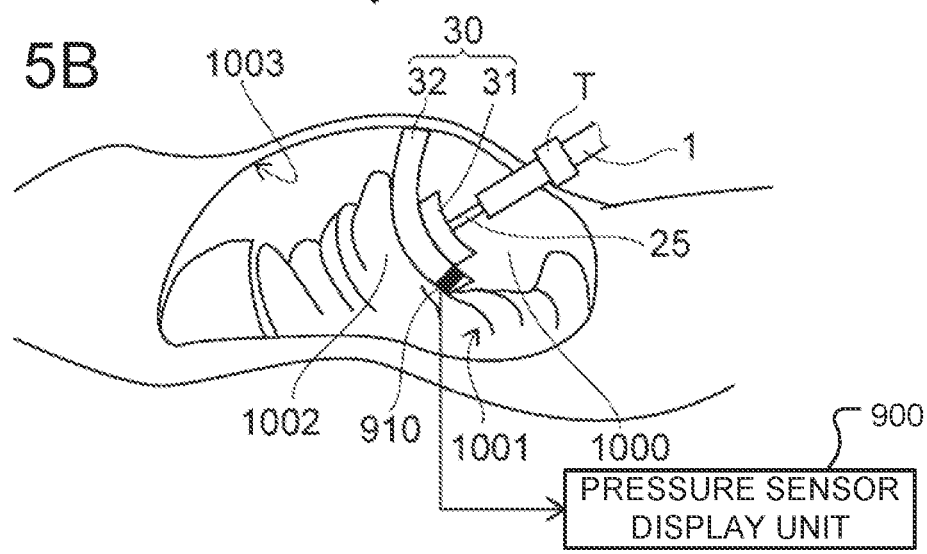

FIG. 5B illustrates a state in which the small intestine 1002 or the like is therefore fixed by the second expandable section 332. The expanded second expandable section 332 hence maintains the state that the large intestine 1001 as the target organ of the surgery is exposed in the field of vision. To confirm that the small intestine 1002 or the like is surely fixed, a pressure sensor 910 may be incorporated in the second expandable section 332. From a pressure value obtained by the pressure sensor 910 and displayed on a pressure sensor display unit 900, the healthcare practitioner can find a force applied to the forceps 20 so that the pressure value can be referred to as an indication as to whether the small intestine 1002 or the like has been reliably retracted or not. As illustrated in FIG. 3, the second expandable section 332 has the fine wave-shaped or concavo-convex shaped portions 33. When pushing aside or retract and fixing the small intestine 1002 or the like, the second expandable section 332 can therefore produce friction to avoid slipping of the small intestine 1002 or the like, thereby enabling to reliably perform the retraction.

Figure 5C:
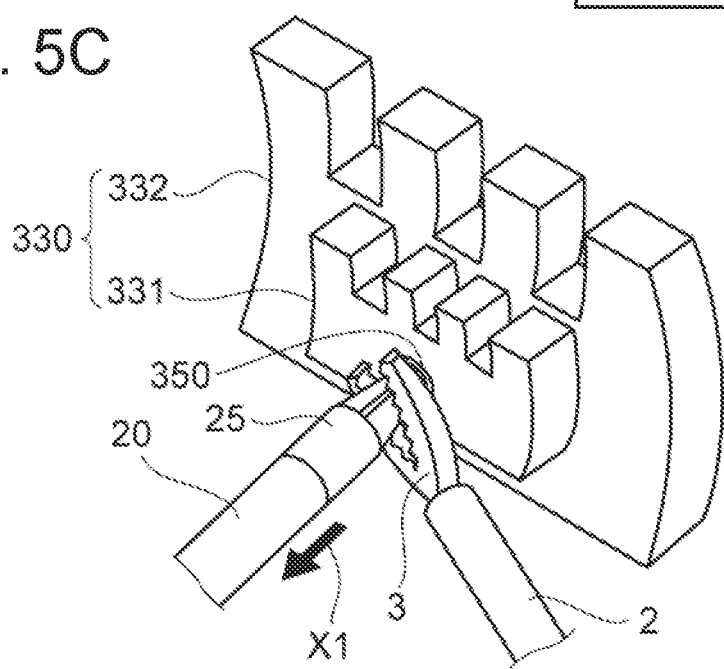

After the fixation of the small intestine 1002 or the like by the second expandable section 332, the expandable body 330, while being kept expanded in the predetermined size and shape, is placed in the abdominal cavity 1000 to maintain the small intestine 1002 or the like in the fixed state. As illustrated by way of example in FIG. 5C, a grasp portion 3 of the additional forceps 2 now grasps the grasp portion 25 of the forceps 20 in the abdominal cavity 1000. The forceps 20 are then pulled out in a direction X1, so that the grasp portion 25 of the forceps 20, the grasp portion 25 closing up the seal structure portion 350, is detached from the seal structure portion 350. Even after the grasp portion 25 is detached from the seal structure portion 350 as described above, the internal fluid does not leak out from the seal structure portion 350 owing to its liquid tight and/or gas tight structure, thereby maintaining the first expandable section 331 and the second expandable section 332 in their expanded states of the predetermined sizes.

As a consequence, the grasp portion 25 of the forceps 20 is detached from the first expandable section 331, whereby the expandable body 330 (e.g., "a balloon," etc.) is placed in the abdominal cavity 1000. As the expandable body 330 has the thin valve structure 351, the fluid does not leak out to the outside from the expandable body 330. Moreover, the placed expandable body 330 has the fine wave-shaped or concavo-convex shaped portions 33, and therefore the friction forces to the abdominal wall 1003 and the organ are enhanced to enable more firm fixing. Furthermore, the expandable body 330 itself can be fixed such that it is firmly squeezed by the belly side and the back side. It is therefore possible to reduce movement of the expandable body 330.

In addition, the first expandable section 331 and the second expandable section 332 have the comb shape or hand shape. Even if the fluid is supplied in the same amount, compared with formation of the expandable sections in rectangular prismatic shapes, the first expandable section 331 can hence be ensured to have great external dimensions for use in the pushing aside or retracting work for the organ, and the second expandable section 332 can also be ensured to have great external dimensions for use in the fixing work for the retracted organ. Accordingly, the first expandable section 331 can easily perform the pushing aside or retracting operation, and the second expandable section 332 can easily perform the fixing operation.

It is to be noted that the forceps 20 detached from the expandable body 330 have the grasp portion 25, and the grasp portion 25 of the forceps 20 can be used in a similar manner as general forceps in the surgery. It is also to be noted that the forceps 20 are configured to have the grasp portion 25 in this embodiment but the present disclosure is not limited to such a configuration. For example, the forceps 20 may be used to perform only operation of the expandable body 330, and once fixation completes, general forceps may be used. In this manner, the forceps 20 can be simplified.

To recover, from the abdominal cavity 1000, the expandable body 330 which is in the state expanded to the predetermined size and shape, the size of the expandable body 330 is made smaller by releasing the fluid from the first expandable section 331 and the second expandable section 332 of the expandable body 330 to cause contraction of the expandable body 330. In this case, the fluid in the first expandable section 331 and the fluid in the second expandable section 332 are released by opening a hole in the expandable body 330 or cutting the expandable body 330, for example, using the grasp portion 25 of the forceps 20. Accordingly, the expandable body 330 itself undergoes elastic contraction, and is allowed to compact and collapse.

After that, the expandable body 330 contracted to the small size can be recovered by grasping it, for example, with the grasp portion 25 of the forceps 20 and taking it out of the body from the abdominal cavity 1000 through the trocar tube T.

Especially, when a carbon dioxide gas is used as the fluid, the expandable body 330 can be taken out using the grasp portion 25 of the forceps 20 after causing contraction of the expandable body 330 by cutting the expandable body 330 at an appropriate part thereof with the grasp portion 25 and discharging the carbon dioxide gas from the expandable body 330 into the abdominal cavity 1000. When physiological saline is used as the fluid, the physiological saline can also be discharged into the abdominal cavity 1000.

In this embodiment, a hole is opened in the expandable body 330 or the expandable body 330 is cut to cause contraction of the expandable body 330. In this disclosure, however, the expandable body 330 may also be configured to draw out a carbon dioxide gas or physiological saline, for example, through the forceps 20 by inserting the forceps 20 again into the seal structure portion 350. In this manner, a carbon dioxide gas or physiological saline can be prevented from flowing out into the abdominal cavity 1000.

FIGS. 6A to 6E illustrate various modifications of some of the elements in the organ retraction device of the first example described above. In FIG. 6A, the first expandable section 331 and second expandable section 332 of the expandable body 330 may be formed from a shape memory material, for example, a nickel-titanium (Ni—Ti) shape memory alloy, a shape memory polymer, or the like instead of the balloon-like structure sections. The forceps 20 are configured to include a heat source 390 in the grasp portion 25 of the forceps 20, and to deliver heat to the first expandable section 331 and the second expandable section 332 by way of a thermal conductor 391. As illustrated in FIG. 6B, when the first expandable section 331 receives a first predetermined quantity of heat (e.g., provided by the heat source) and reaches a first predetermined temperature, the first expandable section 331 expands from a collapsed state to an expanded state. Next, the second expandable section 332 may receive a second predetermined quantity, or amount, of heat (e.g., provided by the heat source) and reaches a second predetermined temperature (e.g., that is higher than the temperature in the abdominal cavity 1000 and the first predetermined temperature provided to the first expandable section 331), the second expandable section 332 expands from a collapsed state to an expanded state.

On the other hand, the first expandable section 331 and second expandable section 332 of the expandable body 330 may use, for example, a shape memory polymer instead of the balloon-like structure bodies. In this case, a shape memory polymer having a glass transition temperature close to the temperature in the abdominal cavity 1000, for example, close to 39° C. may be selected. Heat is delivered from the heat source 390 to the first expandable section 331 and the second expandable section 332 by way of the thermal conductor 391 disposed in the grasp portion 25, so that the first expandable section 331 and the second expandable section 332 are heated to a predetermined temperature that is higher than the temperature in the abdominal cavity 1000 to soften them beforehand. At the temperature in the abdominal cavity 1000, the first expandable section 331 and the second expandable section 332 may then be allowed to maintain their predetermined sizes and shapes, respectively.

Further, in FIG. 6C, an actuator 395 is disposed in the forceps 20. By turning on the actuator 395, the grasp portion 25 and the expandable body 330 grasped by the grasp portion 25 are caused to swing in directions R when pushing aside and fixing, for example, the small intestine or the like. This facilitates application of operative techniques. According to the procedure or operative technique in the surgery, the grasp portion 25 may be detached from the forceps 20, and a suction head 444 may be attached as illustrated in FIG. 6D. This enables to perform suction operation according to the procedure of operative technique in the surgery. According to the procedure or operative technique in the surgery, the grasp portion 25 may be detached from the forceps 20, and an electric scalpel 445 may also be attached as also illustrated in FIG. 6D. This enables use of the electric scalpel 445 according to the procedure or operative technique in the surgery. According to the procedure or operative technique in the surgery, a light source 446 may also be attached to the forceps 20 as also illustrated in FIG. 6D. According to the procedure or operative technique in the surgery, this enables the light source 446 to be used so that a field of vision can be secured. As illustrated in FIG. 6E, the grasp portion 25 may also be connected to the expandable body 330 by inserting the grasp portion 25 into the seal structure portion 350 of the expandable body 330 and turning the grasp portion 25 as in the operation of a key. This enhances the reliability of the connection between the grasp portion 25 and the expandable body 330.

If the expandable body 330 is made, for example, from a bioabsorbable material, specifically a simple substance such as polylactic acid, polyglycolic acid, or polydioxane and/or a composite substance of one or more of such simple substances, the expandable body 330 is absorbed in the body if simply left in the abdominal cavity after contraction. The recovery of the expandable body 330 by taking it out is therefore obviated, so that application of operative techniques can be simplified.

As the expandable body 330, one of expandable bodies of different sizes may be selectable on the basis of test results of computerized tomography (CT) or the like. This enables to use the expandable body 330 conforming to the size of the abdominal cavity of each individual patient, and therefore the reliability of application of operative techniques is increased. After determination of the size of the abdominal cavity, the expandable body 330 may be produced by a three-dimensional (3D) printer. This can facilitate bespoke production of the expandable body 330, the expandable body 330 conforming to the size of the abdominal cavity of each individual patient can be used, and the reliability of application of operative techniques is increased. As the material of the expandable body 330, a material having radiopacity may be used. For example, the expandable body 330 may be covered by surgical gauze with radiopaque threads woven therein. By X-ray imaging after completion of the surgery, it is hence possible to confirm, through images, whether the entirety or a part of the expandable body 330 remains in the abdominal cavity or not.

The expandable body 330 may have, for example, an insulating coating so that it does not puncture even if an electric scalpel comes into contact with the same. This insulating coating may prevent incidents even if an electric scalpel is used during application of operative techniques. In one example, the expandable body 330 may be covered with a water-absorbing material, for example, gauze, or may be made of sponge or the like at a part thereof, where the expandable body 330 comes into contact with the abdominal wall. This water-absorbing material may ensure enhancement of a friction force for the fixation of the expandable body 330 in the abdominal cavity 1000 and a dry environment in the abdominal cavity 1000.

Next, a second example of the organ retraction device of the present disclosure will be described. Where elements of an organ retraction device 1 of the second example are substantially the same as the corresponding elements of the organ retraction device 201 of the first example, these elements are identified by the same reference numerals.

Figure 7:
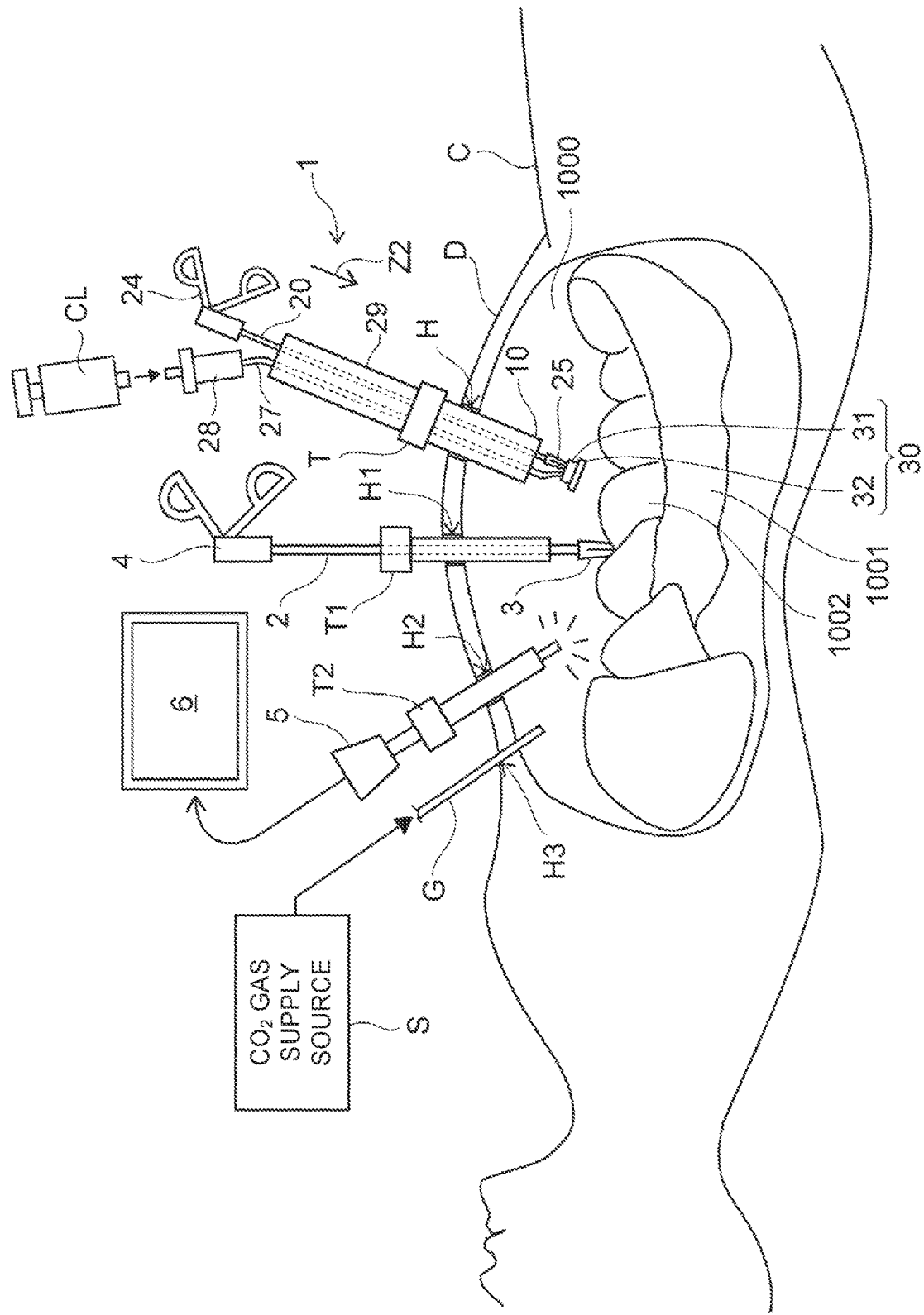
FIG. 7 is a schematic diagram illustrating a second example of the organ retraction device used in a laparoscopic surgery in accordance with examples of the present disclosure.
Figure 8:
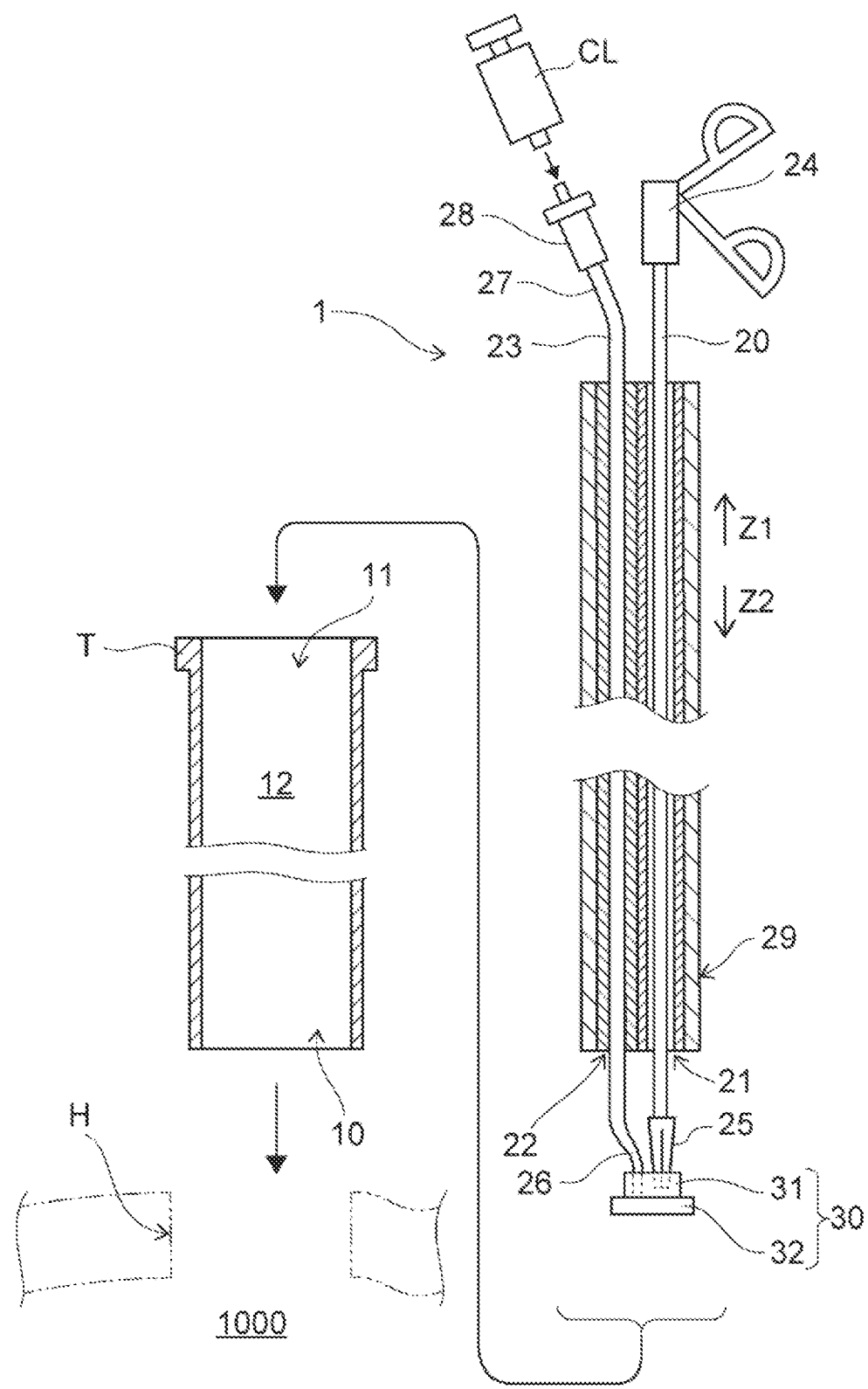
FIG. 8 is a partial cross-sectional front view illustrating a specific configuration example of the organ retraction device illustrated in FIG. 7.

FIG. 7 is a schematic diagram illustrating a second example of the organ retraction device 1 used in a laparoscopic surgery. FIG. 8 is a partial cross-sectional front view illustrating a specific configuration example of the organ retraction device 1 illustrated in FIG. 7.

Referring first to FIGS. 7 and 8, a description will be made about the organ retraction device 1. As illustrated in FIG. 7, the organ retraction device 1 is extractably inserted into the trocar tube T. The organ retraction device 1 pushes aside or retracts another organ that lies over a target organ for the surgery, for example, the large intestine 1001 in a surgery for bowel cancer, for example, the small intestine 1002 or the like to expose the large intestine 1001 as the target organ for the surgery. The organ retraction device 1 then fixes the retracted other organ, for example, the small intestine 1002 and/or the like to avoid its dislocation, or movement, in the abdominal cavity 1000 (e.g., during surgery, etc.).

In FIG. 8, the organ retraction device 1, the abovementioned trocar tube T, and an incision site H are illustrated. The trocar tube T is extractably inserted into the incision site H. The one end portion (e.g., inner end portion) of the trocar tube T serves as the distal end opening 10, while the other end portion (e.g., outer end portion) of the trocar tube T serves as the insertion opening 11. The distal end opening 10 and the insertion opening 11 are communicated to each other via the insertion passage 12. The distal end opening 10 is placed in the abdominal cavity 1000. The insertion passage 12 has an inner diameter of a size large enough to permit extractable insertion of the organ retraction device 1. When using the organ retraction device 1, the organ retraction device 1 is inserted on a side of a distal end portion thereof from the insertion opening 11, through the insertion passage 12, and from the distal end opening 10 of the trocar tube T into the abdominal cavity 1000.

In FIG. 8, a specific configuration example of the organ retraction device 1 is illustrated. The organ retraction device 1 includes the forceps 20, a first lumen 21, a second lumen 22, a catheter 23, a sheath member 29, and an expandable body 30. The forceps 20 are an example of the surgical instrument. The sheath member 29 covers around the first lumen 21 and the second lumen 22, and holds the first lumen 21 and the second lumen 22 together as integral elements. The sheath member 29 is, for example, a plastic-made tubular member. The first lumen 21 and the second lumen 22 are tubular or cylindrical members having a cavity inside, and are, for example, plastic-made tubular members.

As illustrated in FIGS. 7 and 8, the forceps 20 have been inserted through the first lumen 21. The first lumen 21 has an inner diameter of a size large enough to permit insertion of the grasp portion 25 of the forceps 20 and the expandable body 30 in the below-described collapsed state therethrough. The forceps 20 are therefore configured such that, by inserting the grasp portion 25 and the expandable body 30, which is grasped in the collapsed state by the grasp portion 25, in a direction Z2 into the first lumen 21, the grasp portion 25 and the expandable body 30 can be inserted into the abdominal cavity 1000 through the first lumen 21.

The forceps 20 have the hand control part 24 and the grasp portion 25. The grasp portion 25 is disposed at the one end portion (e.g., inner end portion) of the forceps 20, while the hand control part 24 is disposed at the other end portion (e.g., outer end portion) of the forceps 20. The grasp portion 25 can be operated to open or close by manipulation of the hand control part 24. When a healthcare practitioner manipulates the hand control part 24, the grasp portion 25 is operated open or closed. The expandable body 30 is grasped by the grasp portion 25, and the grasp portion 25 is detachably, liquid-tightly, and/or gas-tightly connected to the expandable body 30. The expandable body 30 is in the collapsed state.

As illustrated in FIG. 8, the catheter 23 is, for example, a plastic-made, flexible tubular member. A catheter is a flexible slender tube to be inserted into the body, and may be made, for example, from a high molecular compound such as nylon or silicone. The catheter 23 is inserted in the second lumen 22. The catheter 23 is detachably, liquid-tightly, and/or gas-tightly connected at one end portion (e.g., inner end portion) 26 thereof to the expandable body 30 in the abdominal cavity 1000. The catheter 23 has the connector portion 28 at the other end portion (e.g., outer end portion) 27 thereof. The connector portion 28 is connected to the fluid supplier CL such as a syringe. This fluid supplier CL supplies the fluid into the expandable body 30 through the catheter 23, whereby the expandable body 30 in the collapsed state is expanded, and is allowed to hold an expanded state. Examples of the fluid which the fluid supplier CL supplies may include, but are in no way limited to, gases such as a carbon dioxide gas and air, and liquids such as physiological saline.

Figure 9:
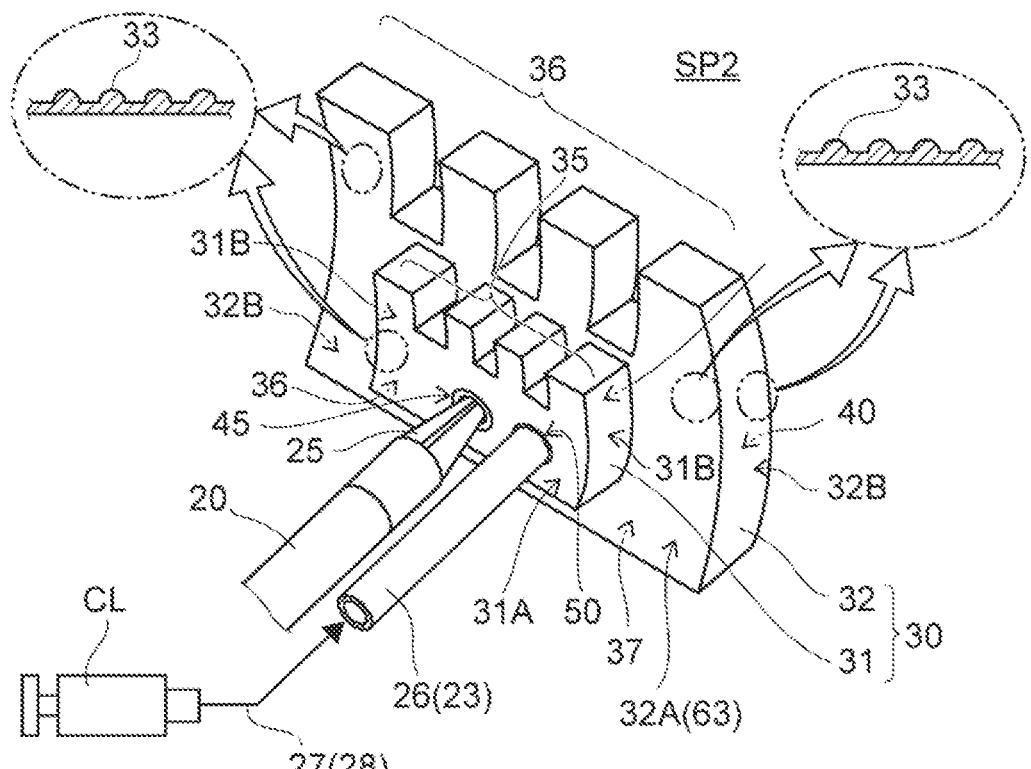
FIG. 9 is a schematic diagram illustrating an expandable body of the organ retraction device illustrated in FIG. 8 in a state where the expandable body is expanded to a predetermined size and shape in accordance with examples of the present disclosure.
Figure 10A:
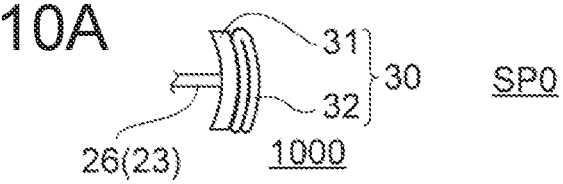
FIGS. 10A to 10C are views illustrating the expandable body of the organ retraction device illustrated in FIG. 8, in which the expandable body expands from a collapsed state to an expanded state as illustrated in FIG. 9.
Figure 10B:
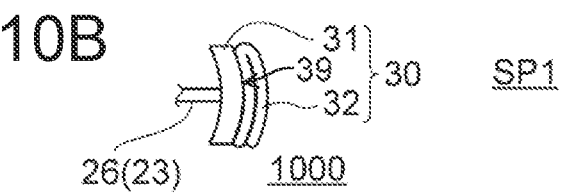
Figure 10C:
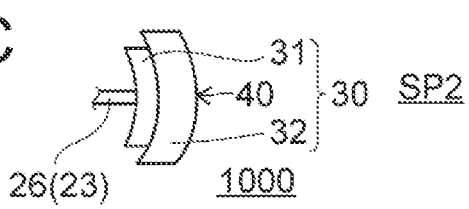

Referring to FIGS. 8 to 10C, the expandable body 30 will be described next. FIG. 9 is a view illustrating the expandable body 30 in a state expanded to a predetermined size and shape, and FIGS. 10A to 10C are views illustrating the expandable body 30 expanded from the collapsed state to the expanded state as illustrated in FIG. 9. FIG. 10A illustrates the collapsed state, in which the first expandable section 31 and the second expandable section 32 of the expandable body 30 are in collapsed states before injection of the fluid (e.g., this state may be referred to herein as the "preliminary stage SP0"). FIG. 10B illustrates a state, in which only the first expandable section 31 is expanded to a predetermined size and shape by injection of the fluid and the second expandable section 32 is still in the collapsed state (e.g., this state may be referred to herein as the "first stage SP1"). Further, FIG. 10C illustrates a state, in which the first expandable section 31 and the second expandable section 32 are both expanded to predetermined sizes and shapes, respectively, by injection of the fluid into the first expandable section 31 and the second expandable section 32 (e.g., this state may be referred to herein as the "second stage SP2").

The expandable body 30 illustrated in FIG. 9 comprises the first expandable section 31 and the second expandable section 32. The first expandable section 31 and the second expandable section 32 are integral together. By beginning to inject the fluid into the collapsed first expandable section 31 in the preliminary stage SP0 as illustrated in FIG. 10A, only the first expandable section 31 expands to the predetermined size and shape when the fluid is injected to a predetermined pressure or predetermined amount in the first stage SP1 illustrated in FIG. 10B. However, the second expandable section 32 still remains in the collapsed state. When the fluid is further injected to a predetermined pressure or predetermined amount in the first stage SP1 illustrated in FIG. 10B, the second expandable section 32 is expanded to a predetermined size and shape in the second stage SP2 illustrated in FIG. 10C while the first expandable section 31 is maintained in the expanded state.

As means for injecting the fluid, the fluid supplier CL illustrated in FIGS. 7 and 9 may be used, for example. As illustrated in FIG. 8, the fluid supplier CL is detachably connected to the connector portion 28 of the catheter 23. The fluid supplier CL is configured such that, when a healthcare practitioner depresses the push part (e.g., plunger, etc.) of the fluid supplier CL (e.g., syringe, etc.), the predetermined amount of the fluid in the fluid supplier CL is supplied to a side of the expandable body 30 through the connector portion 28 and one end portion 26 of the catheter 23. A mechanism for injecting the fluid into the first expandable section 31 and the second expandable section 32, will be subsequently described herein.

Taking a laparoscopic surgery for bowel cancer as an example, the first expandable section 31 plays a role to push aside or retract the other organ (e.g., the small intestine 1002, and/or the like) that lies over the target organ (e.g., the large intestine 1001) for the surgery as illustrated in FIG. 7, and to expose the target organ (e.g., the large intestine 1001) for the surgery. On the other hand, the second expandable section 32 plays a role to fix the retracted other organ, for example, the small intestine 1002 or the like to avoid its dislocation, or movement, in the abdominal cavity 1000 (e.g., during the surgery). For this purpose, the volume of the second expandable section 32 of the expandable body 30 in the state that the second expandable section 32 is expanded may be set greater than the volume of the first expandable section 31 in its expanded state to fix the retracted other organ without dislocation in the abdominal cavity 1000.

As illustrated in FIG. 9, the first expandable section 31 and the second expandable section 32 may be formed in a comb shape or hand shape in the states that the first expandable section 31 and the second expandable section 32 have expanded in the vicinity of the distal end opening 10 of the trocar tube T illustrated in FIGS. 7 and 8. Even if the fluid is supplied in the same amount, compared with formation of the expandable sections in rectangular prismatic shapes, the first expandable section 31 can be ensured to have great external dimensions for use in the pushing aside or retracting work for the organ, and the second expandable section 32 can be ensured to have great external dimensions for use in the fixing work for the organ. The first expandable section 31 and the second expandable section 32 may be formed of an elastically deformable, thin plastic or rubber film, so that the first expandable section 31 and the second expandable section 32 easily expand when the fluid is injected and contract into the collapsed states when the fluid is released conversely.

As illustrated in FIG. 9, the first expandable section 31 has the attachment surface 31A, the left and right side surfaces 31B and 31B, the upper comb portion 35, and the bottom surface portion 37. Similarly, the second expandable section 32 has the inner surface portion 32A, the left and right side surfaces 32B, the upper comb portion 36, the bottom surface portion 37, and the pressing surface portion 40. The first expandable section 31 and the second expandable section 32 each have a curved shape. The attachment surface 31A and the inner surface portion 32A are formed as concave surfaces. The pressing surface portion 40 is formed as a convex surface. The first expandable section 31 is curved, and therefore can push aside or retract the organ while pushing it up. The second expandable section 32 is also curved, and therefore can fix the retracted organ in the pushed-up state. Owing to these features, it is therefore possible to secure a field of vision as needed during the surgery.

In the first stage SP1 of FIG. 10B, the first expandable section 31 is expanded in the vicinity of the trocar tube T, but the second expandable section 32 is not expanded and is collapsed, as illustrated in FIGS. 7 and 8. In this state, the pressing surface portion 39, which is formed as a convex surface, of the first expandable section 31 plays a role to push aside or retract the other organ (e.g., the small intestine 1002, and/or the like) that lies over the target organ (e.g., the large intestine 1001) for the surgery. As illustrated in FIG. 10C, the first expandable section 31 and the second expandable section 32 have been both expanded in the second stage SP2, so that the pressing surface portion 40 plays a role to fix the retracted other organ, for example, the small intestine 1002 or the like to avoid its dislocation in the abdominal cavity 1000.

As illustrated in FIG. 9, the first expandable section 31 has a connection port 45 and a fluid injection port 50 on a side of the attachment surface 31A. The grasp portion 25 of the forceps 20 is inserted in the connection port 45. In this state, the grasp portion 25 detachably grasps the first expandable section 31. The grasp portion 25 is liquid-tightly and gas-tightly connected to the connection port 45. The connection port 45 is closed up by the grasp portion 25 as described above, so that the fluid injected into the first expandable section 31 does not leak from the connection port 45. The one end portion 26 of the catheter 23 is detachably, liquid-tightly, and/or gas-tightly connected to the fluid injection port 50 of the expandable body 30 in the abdominal cavity 1000. The fluid can therefore be injected into the first expandable section 31 through the one end portion 26 of the catheter 23 without leakage at the fluid injection port 50.

As illustrated in FIG. 9, the first expandable section 31 and the second expandable section 32 may have, at the surfaces thereof, fine wave-shaped or concavo-convex shaped portions 33. Accordingly, the expandable body 30 can reliably perform the pushing aside or retraction of an organ other than the large intestine 1001, for example, the small intestine 1002 or the like to have the large intestine 1001 exposed as the target organ for the surgery, and also the fixation of the retracted small intestine 1002 or the like to avoid its dislocation in the abdominal cavity 1000. In particular, at least the pressing surface portion 40 may be provided with the fine wave-shaped or concavo-convex shaped portion 33. This enables to more reliably fix the retracted small intestine 1002 or the like to avoid its dislocation in the abdominal cavity 1000.

Referring next to FIGS. 11A to 11C, structural examples of the connection port 45 and the fluid injection port 50 of the first expandable section 31 will be described. FIG. 11A illustrates an example structure of the connection port 45. FIGS. 11B and 11C illustrate an example structure of the fluid injection port 50.

In FIG. 11A, the attachment surface 31A of the first expandable section 31 is illustrated, and the grasp portion 25 of the forceps 20 is inserted and fixed in the connection port 45 disposed in the attachment surface 31A so that the grasp portion 25 does not come off easily. The grasp portion 25 includes hooks 25F. With the grasp portion 25 inserted in the connection port 45, the grasp portion 25 is fixed relative to the attachment surface 31A by a large-diameter portion 25T and the hooks 25F of the grasp portion 25 so that the grasp portion 25 is prevented from detachment in a direction X.

As illustrated in FIG. 11A, a surrounding portion 31C is disposed on an inner surface on a side opposite to the attachment surface 31A so that the distal end portion of the grasp portion 25 is surrounded. A thin wall portion 31D is centrally formed in the surrounding portion 31C. Owing to the inclusion of the surrounding portion 31C, gas tightness and/or liquid tightness is ensured around the connection port 45. In a case of detaching the grasp portion 25 from the connection port 45, however, it is only necessary to simply pull out the grasp portion 25 in a direction X1. As a result, the hooks 25F are forcedly pulled out of the connection port 45.

In the first stage SP1 of FIG. 11B and the second stage SP2 of FIG. 11C, the one end portion 26 of the catheter 23 is detachably, liquid-tightly, and/or gas-tightly connected to the fluid injection port 50 in the attachment surface 31A of the first expandable section 31 in the abdominal cavity 1000. The catheter 23 has a flange portion 26F at the one end portion 26 thereof. The flange portion 26F is fixed by a fixing member 31H on the inner surface on the side opposite to the attachment surface 31A. The flange portion 26F does not come off in the direction X from the fluid injection port 50. In a case of detaching the flange portion 26F from the attachment surface 31A, however, it is only necessary to simply pull out the one end portion 26 of the catheter 23 in the direction X1. As a result, the flange portion 26F is forcedly pulled out of the fluid injection port 50.

As illustrated in FIG. 11B, a check valve 60 is disposed on the fixing member 31H. The check valve 60 has fluid flow openings 61 and a spherical valve element 62 (e.g., ball, etc.). The spherical valve element 62 is movable in the direction X within the check valve 60. When the fluid flows from the one end portion 26 of the catheter 23 into the check valve 60 as indicated by an arrow E, the fluid is injected into the first expandable section 31 by way of the fluid flow openings 61. The first expandable section 31 is therefore expanded to a predetermined volume as illustrated in FIGS. 10A to 11B. When the supply of the fluid is stopped, the spherical valve element 62 moves leftward by the pressure of the fluid in the first expandable section 31, and closes up the fluid flow openings 61. When as described above, the injection of the fluid is stopped and the first expandable section 31 is expanded, the spherical valve element 62 moves leftward (e.g., in the direction X1) and closes up the fluid flow openings 61 so that the expanded state of the first expandable section 31 is maintained in the predetermined size and shape.

As illustrated in FIG. 11B, a partition 63 is disposed to divide the first expandable section 31 and the second expandable section 32 from each other. The partition 63 has a fluid flow opening 64, and a check valve 65. The check valve 65 has fluid flow openings (e.g., orifices) 66 defined by communication openings smaller than the fluid flow opening 64, and a spherical valve element 67 (e.g., ball, etc.). In one example, a biasing member, for example, a coil spring (not illustrated) may also be disposed to urge the spherical valve element 67 leftward by a predetermined pushing force. When the fluid further flows into the check valve 60 as indicated by the arrow E from the one end portion 26 of the catheter 23 via the fluid flow openings 61 as illustrated in FIGS. 11B to 11C, the fluid is injected into the first expandable section 31 by way of the fluid flow openings 61, and then flows into the second expandable section 32 by way of the fluid flow opening 64 and the fluid flow openings 66. As illustrated in FIGS. 11B to 11C, the second expandable section 32 is therefore expanded to a predetermined volume. As the injection of the fluid is stopped and the first expandable section 31 and the second expandable section 32 are expanded, the spherical valve element 67 moves leftward (e.g., in the direction X1) by the pressure of the fluid in the second expandable section 32, and closes up the fluid flow openings 66 and 64. On the other hand, the spherical valve element 62 also moves leftward by the pressure of the fluid in the first expandable section 31, and closes up the fluid flow openings 61 and 50. The expanded states of the first expandable section 31 and the second expandable section 32 are hence maintained in the predetermined sizes and shapes.

Using an example in which the above-mentioned organ retraction device 1 is applied to a laparoscopic surgery for bowel cancer, a method of use of the organ retraction device 1 will be described next.

As illustrated in FIGS. 7 and 8, the expandable body 30 is collapsed small at the beginning, and is grasped by the grasp portion 25 of the forceps 20. As illustrated in FIG. 7, the trocar tube T is inserted into the incision site H, and the forceps 20 and the expandable body 30 of the organ retraction device 1 are inserted into the abdominal cavity 1000 through the trocar tube T.

When a pushing-aside operation is performed with the expandable body 30 in retraction, an organ other than the large intestine 1001, for example, the small intestine 1002 and/or the like is pushed aside to have the large intestine 1001 exposed as the target organ for the surgery. When the fluid flows into the check valve 60 from the one end portion 26 of the catheter 23 as indicated by the arrow E illustrated in FIG. 11B, the fluid is injected into the first expandable section 31 by way of the fluid flow openings 61.

Figure 12A:
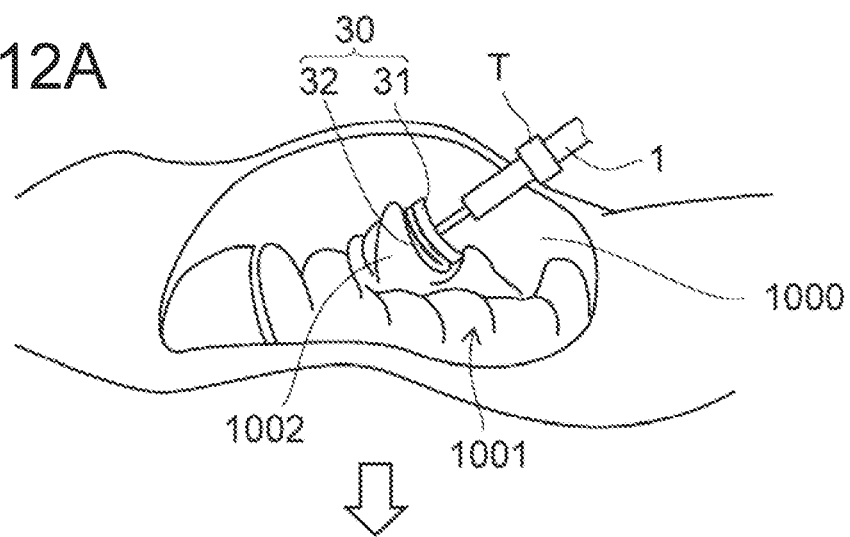
FIGS. 12A to 12C are views illustrating a pushing aside or retracting operation of an organ, a fixing operation of the organ, and a manner of detaching a pair of forceps from the expandable body when the expandable body is placed in the abdominal cavity, respectively, all, using the organ retraction device illustrated in FIG. 7.

As illustrated in FIG. 10A to FIG. 11B, the first expandable section 31 is expanded to a predetermined volume. FIG. 11A illustrates a state in which only the first expandable section 31 of the expandable body 30 is expanded to the predetermined size and shape. When the healthcare practitioner manipulates the hand control part 24 of FIG. 7, the first expandable section 31 pushes aside the small intestine 1002 or the like in the abdominal cavity 1000 as illustrated by way of example in FIG. 12A. The first expandable section 31 is then placed at a predetermined site in the abdominal cavity 1000 by operation of the grasp portion 25 of the forceps 20. The large intestine 1001 as the target organ for the surgery is therefore exposed in the field of vision.

Next, the retracted small intestine 1002 and/or the like is fixed, or prevented from moving, to avoid its dislocation during the surgery. If the fluid now flows further into the check valve 60 from the one end portion 26 of the catheter 23 as indicated by the arrow E in FIGS. 11B to 11C, the predetermined amount of the fluid is injected into the first expandable section 32 by way of the fluid flow openings 61, and flows into the second expandable section 32 by way of the fluid flow opening 64 and the fluid flow openings 66.

Figure 12B:
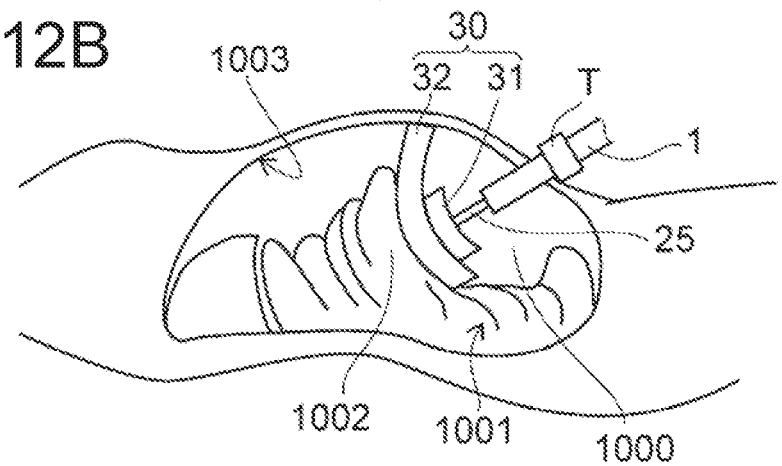

Therefore, the second expandable section 32 is expanded to the predetermined pressure or predetermined amount as illustrated in FIGS. 11B to 11C. FIG. 12B illustrates a state in which the small intestine 1002 or the like is fixed, or prevented from moving from a specific position, by the second expandable section 32. The expanded second expandable section 32 hence maintains the state that the large intestine 1001 as the target organ of the surgery is exposed in the field of vision. As illustrated in FIG. 9, the first expandable section 31 and the second expandable section 32 have the fine wave-shaped or concavo-convex shaped portions 33. When pushing aside or retracting and fixing the small intestine 1002 or the like, the first expandable section 31 and the second expandable section 32 can therefore produce friction to avoid slipping of the small intestine 1002 or the like, thereby enabling to reliably perform the retraction.

After the fixation of the small intestine 1002 or the like by the second expandable section 32, the expandable body 30, while being maintained in the expanded predetermined size and shape, is placed in the abdominal cavity 1000 to maintain the small intestine 1002 and/or the like in the fixed state. As illustrated by way of example in FIG. 12C, a grasp portion 3 of the additional forceps 2 now grasps the grasp portion 25 of the forceps 20 in the abdominal cavity 1000. The forceps 20 may then be pulled out in a direction X1, so that the grasp portion 25 of the forceps 20, the grasp portion 25 closing up the connection port 45, is detached from the connection port 45. Even after the grasp portion 25 is detached from the connection port 45 as described above, the internal fluid does not leak out from the connection port 45 as illustrated in FIG. 11A, thereby maintaining the first expandable section 31 and the second expandable section 32 in their expanded states of the predetermined sizes and shapes.

As a consequence, the grasp portion 25 of the forceps 20 is detached from the first expandable section 31, whereby the expandable body 30 (e.g., "a balloon," etc.) is placed in the abdominal cavity 1000. The placed expandable body 30 has the fine wave-shaped or concavo-convex shaped portions 33, and therefore can be fixed by friction relative to the abdominal wall 1003 and the organ. Furthermore, the expandable body 30 itself is firmly squeezed at upper and lower parts thereof by the abdominal wall 1003 and the organ, and therefore the expandable body 30 does not move.

In addition, the first expandable section 31 and the second expandable section 32 have the comb shape or hand shape. Even if the fluid is supplied in the same amount, compared with formation of the expandable sections in rectangular prismatic shapes, the first expandable section 331 can hence be ensured to have great external dimensions for use in the pushing aside or retracting work for the organ, and the second expandable section 32 can also be ensured to have great external dimensions for use in the fixing work for the retracted organ.

Figure 13:
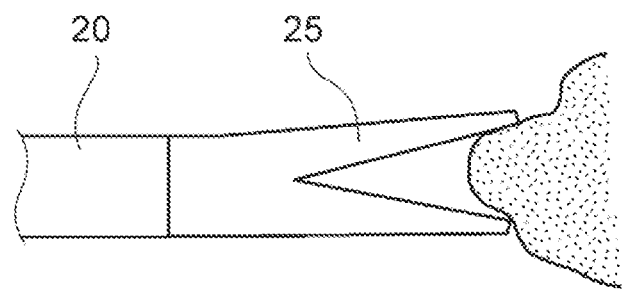
FIG. 13 is a schematic diagram illustrating a manner of using the pair of forceps detached in FIG. 12C.

It is to be noted that, as illustrated in FIG. 13, the forceps 20 detached from the expandable body 30 have the grasp portion 25, and the grasp portion 25 can be used in a similar manner as general forceps in the surgery.

To recover, from the abdominal cavity 1000, the expandable body 30 which is in the state expanded to the predetermined size and shape, the size of the expandable body 30 may need to be made smaller by releasing the fluid from the first expandable section 31 and second expandable section 32 of the expandable body 30.

Figure 14A:
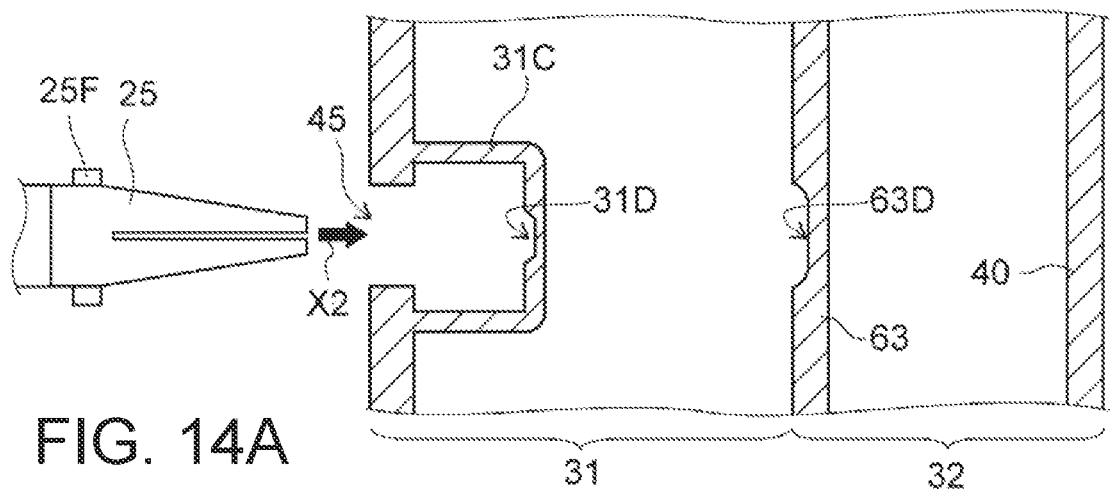
FIGS. 14A to 14C are schematic diagrams illustrating an example of a manner of releasing a fluid such as air from the expanded expandable body to cause contraction of the expandable body illustrated in FIG. 9.
Figure 14B:
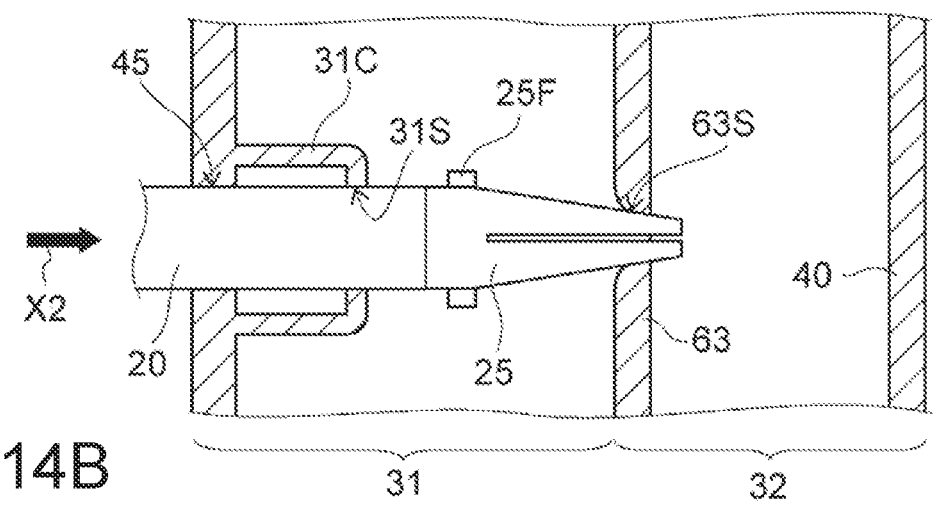
Figure 14C:
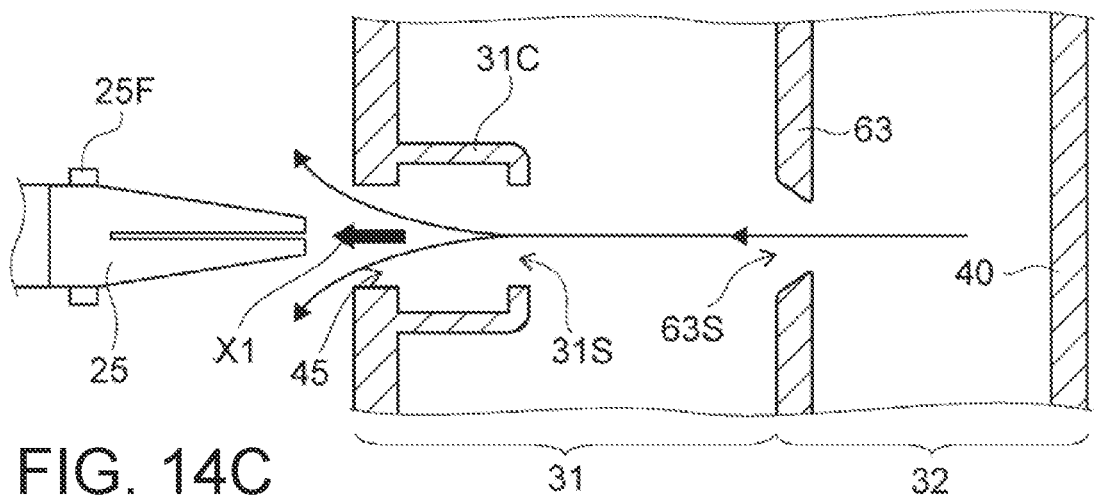

An example in which a gas such as a carbon dioxide gas or air is released from the expandable body 30 is illustrated in FIGS. 14A to 14C. FIG. 14A illustrates a state in which the first expandable section 31 and the second expandable section 32 are expanded. In FIG. 14B, by manipulating the hand control part 24 illustrated in FIG. 7, the grasp portion 25 of the forceps 20 is inserted deep in a direction X2 through the connection port 45. Therefore, the grasp portion 25 breaks through the thin wall portion 31D to form a hole 31S, and also breaks through a thin wall portion 63D of the partition 63 to form a hole 63S.

Figure 15A:
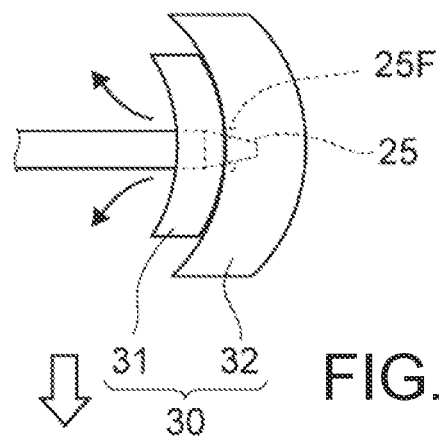
FIGS. 15A to 15D are schematic diagrams illustrating a manner of releasing the fluid, such as air, from the expanded expandable body and causing the expandable body to contract as illustrated in FIGS. 14A to 14C, and recovering the contracted expandable body from the interior of the abdominal cavity in accordance with examples of the present disclosure.
Figure 15B:
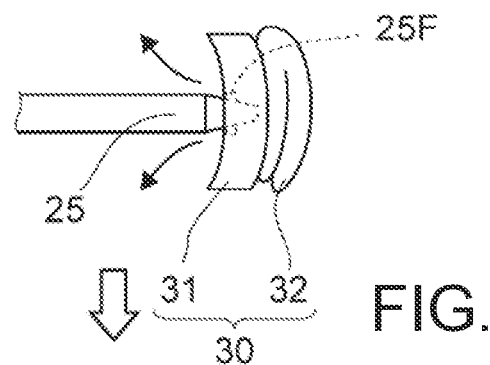

As illustrated in FIG. 14C, the grasp portion 25 of the forceps 20 is then pulled out in the direction X1. As a consequence, the fluid in the first expandable section 31 and the fluid in the second expandable section 32 are released outside from the first expandable section 31 and the second expandable section 32 by way of the hole 31S, the hole 63S, and the connection port 45. Accordingly, the expandable body 30 itself undergoes elastic contraction, and is allowed to compact and collapse, as illustrated in FIGS. 15A, 15B, and 15C.

Figure 12C:
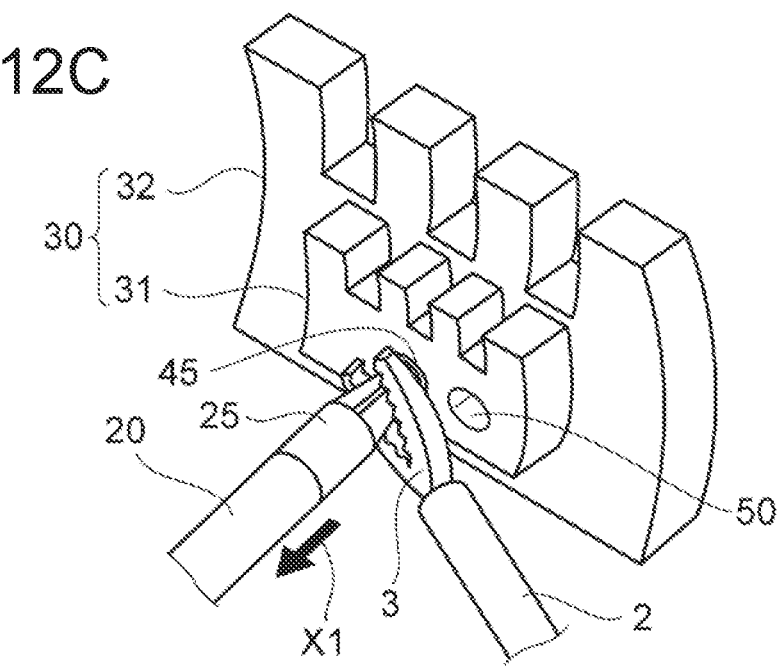
Figure 15C:
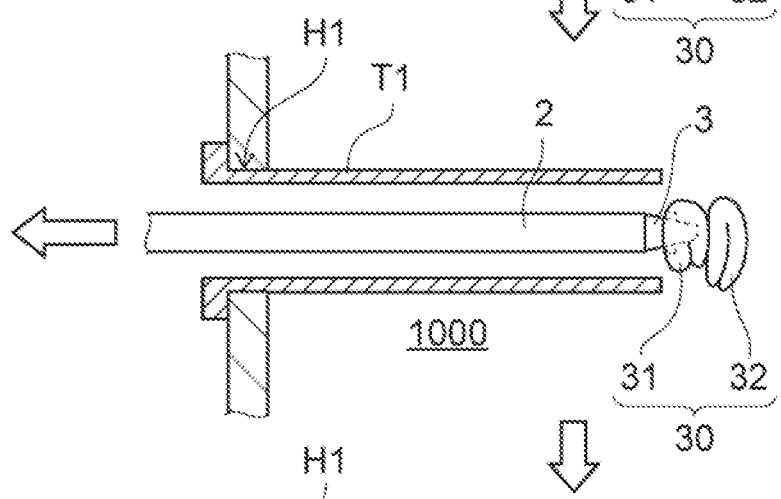
Figure 15D:
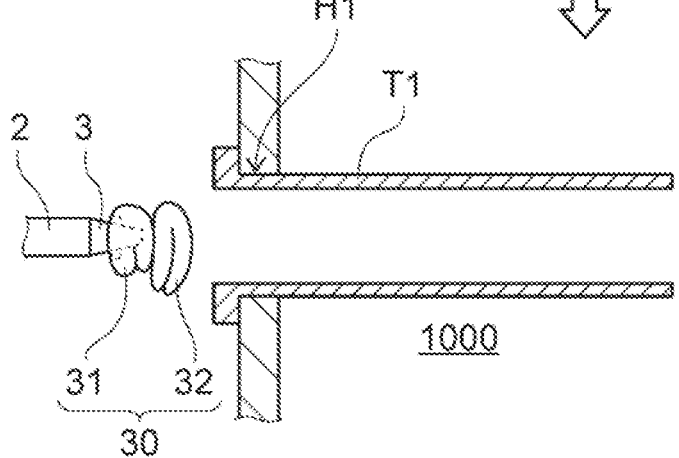

After that, the compacted expandable body 30 can be recovered by grasping it, for example, with the grasp portion 3 of the forceps 2 illustrated, for example, in FIGS. 7, 15C and 15D, and taking it out of the body from the abdominal cavity 1000 through the trocar tube T. As an alternative, the compacted expandable body 30 can also be recovered by grasping it with the grasp portion 25 of the additional forceps 20, which are illustrated in FIG. 12C, instead of the grasp portion 3 of the forceps 2 and taking it out of the body from the abdominal cavity 1000.

When a carbon dioxide gas is used as the fluid, the expandable body 30 may be taken out using the grasp portion 25 of the forceps 20 after causing contraction of the expandable body 30 by cutting the expandable body 30 at an appropriate part thereof with the grasp portion 25 and discharging the carbon dioxide gas from the expandable body 30 into the abdominal cavity 1000. When physiological saline is used as the fluid, the physiological saline can also be discharged into the abdominal cavity 1000 (e.g., without adversely affecting the patient, etc.).

Figure 16:
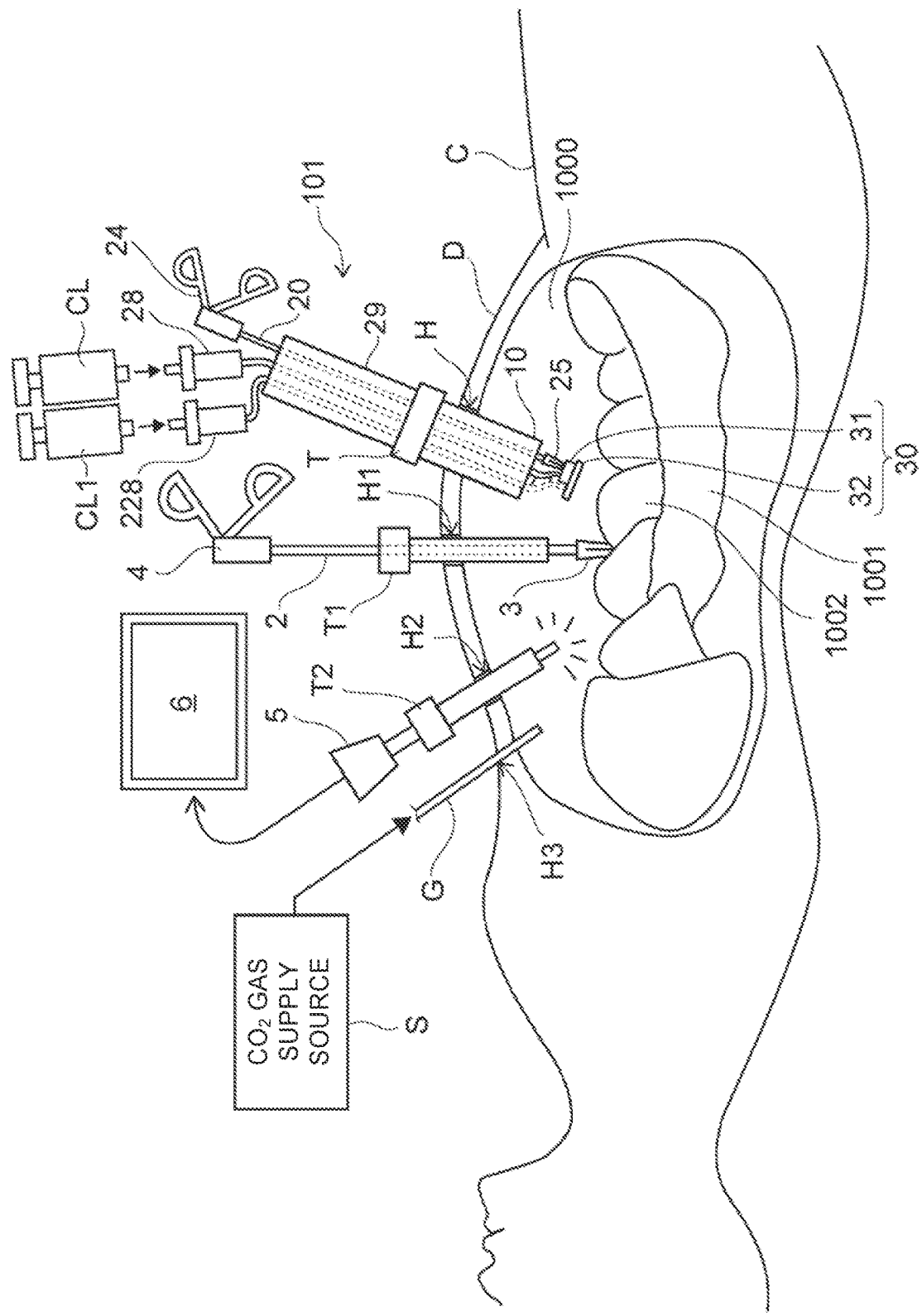
FIG. 16 is a schematic diagram illustrating a third example of the organ retraction device used in a laparoscopic surgery in accordance with examples of the present disclosure.
Figure 17:
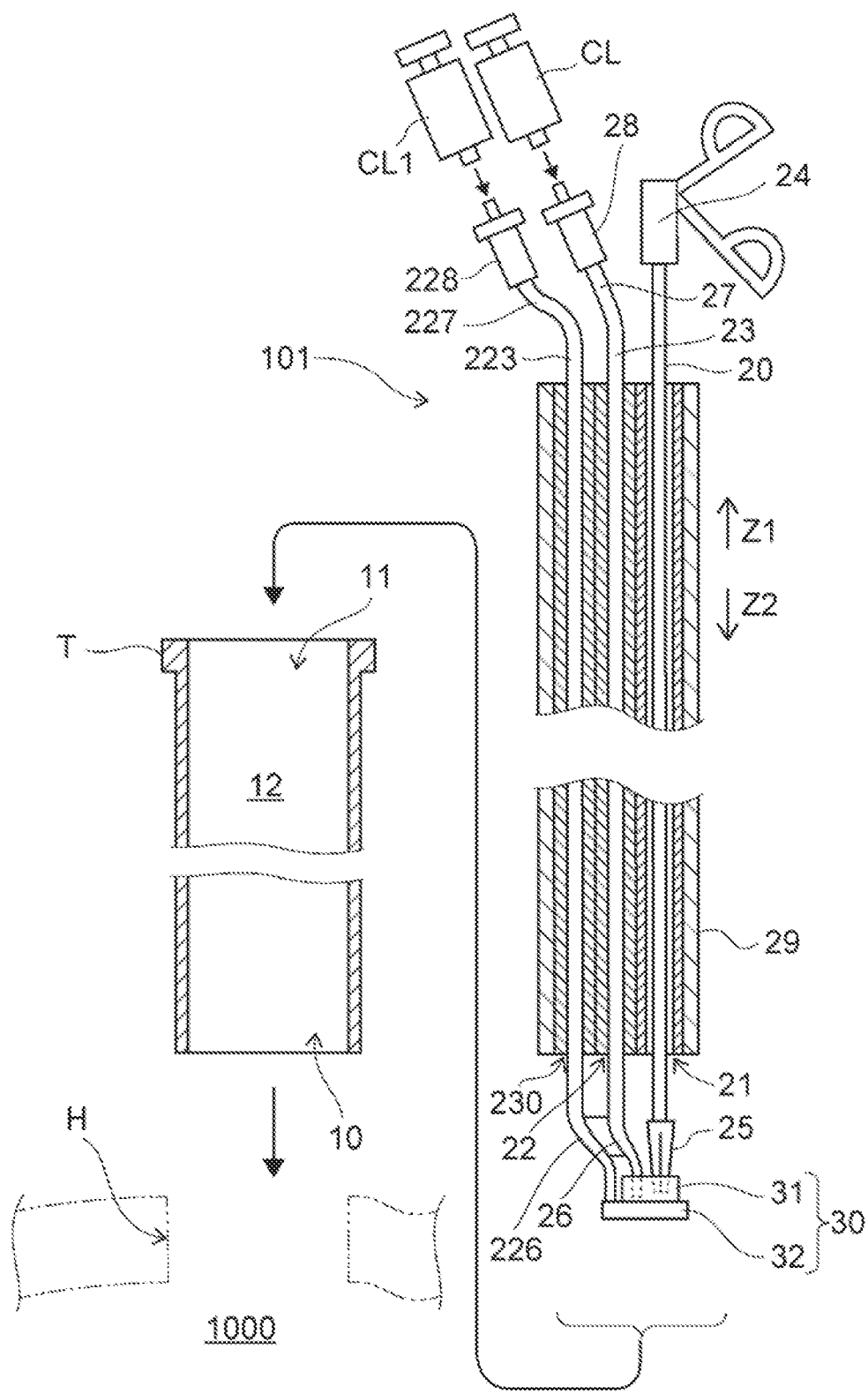
FIG. 17 is a partial cross-sectional front view illustrating a configuration example of the organ retraction device illustrated in FIG. 16.

Next, a third example of the organ retraction device of the present disclosure will be described.

Where elements of an organ retraction device 101 of the third embodiment are substantially the same as the corresponding elements of the organ retraction device 201 of the first embodiment and the organ retraction device 1 of the second embodiment, these elements are identified by the same reference numerals. The organ retraction device 101 of the third embodiment as illustrated in FIGS. 16 to 19 may be different from the organ retraction device 1 of the second embodiment as illustrated in FIGS. 7 to 9 in that some elements may be added. Therefore, a description will hereinafter be made especially centering around the added elements in the organ retraction device 101. FIG. 16 is a schematic diagram illustrating a third example of the organ retraction device used in a laparoscopic surgery in accordance with examples of the present disclosure. FIG. 17 is a partial cross-sectional front view illustrating a configuration example of the organ retraction device 101 illustrated in FIG. 16.

Similar to the organ retraction device 1 illustrated in FIGS. 7 and 8, the organ retraction device 101 illustrated in FIGS. 16 and 17 is extractably inserted into the trocar tube T. The organ retraction device 101 pushes aside or retracts another organ (e.g., the small intestine 1002, etc.) that lies over a target organ (e.g., the large intestine 1001) for a surgery. For example, in a surgery for bowel cancer, for example, the small intestine 1002 or the like may be pushed aside or retracted by the organ retraction device 101 to expose the large intestine 1001 as the target organ for the surgery. The organ retraction device 101 then fixes the retracted small intestine 1002 or the like to avoid its dislocation, or movement, in the abdominal cavity 1000.

In FIG. 17, the organ retraction device 101, the abovementioned trocar tube T, and an incision site H are illustrated. The trocar tube T is extractably inserted into the incision site H. The one end portion (e.g., inner end portion) of the trocar tube T serves as the distal end opening 10, and the distal end opening 10 is placed in the abdominal cavity 1000. The insertion passage 12 has an inner diameter of a size large enough to permit extractable insertion of the organ retraction device 101. When using the organ retraction device 101, the organ retraction device 101 is inserted from the insertion opening 11, is moved forward through the insertion passage 12, and is pushed from the distal end opening 10 of the trocar tube T into the abdominal cavity 1000.

In FIG. 17, the organ retraction device 101 includes the forceps 20, the first lumen 21, the second lumen 22, a third lumen 230, the catheter 23, a catheter 223, the sheath member 29, and the expandable body 30. The forceps 20 are an example of the surgical instrument. The sheath member 29 covers around the first lumen 21, the second lumen 22, and the third lumen 230, and holds the first lumen 21, the second lumen 22, and the third lumen 230 together as integral elements.

The first lumen 21, the second lumen 22, and the third lumen 230 are tubular or cylindrical members having a cavity inside, and are, for example, plastic-made tubular members. It is to be noted that, in the following description, the catheter 23 will be referred to as "the first catheter 23," and the catheter 223 will be referred to as "the second catheter 223," for the sake of their differentiation.

Figure 18:
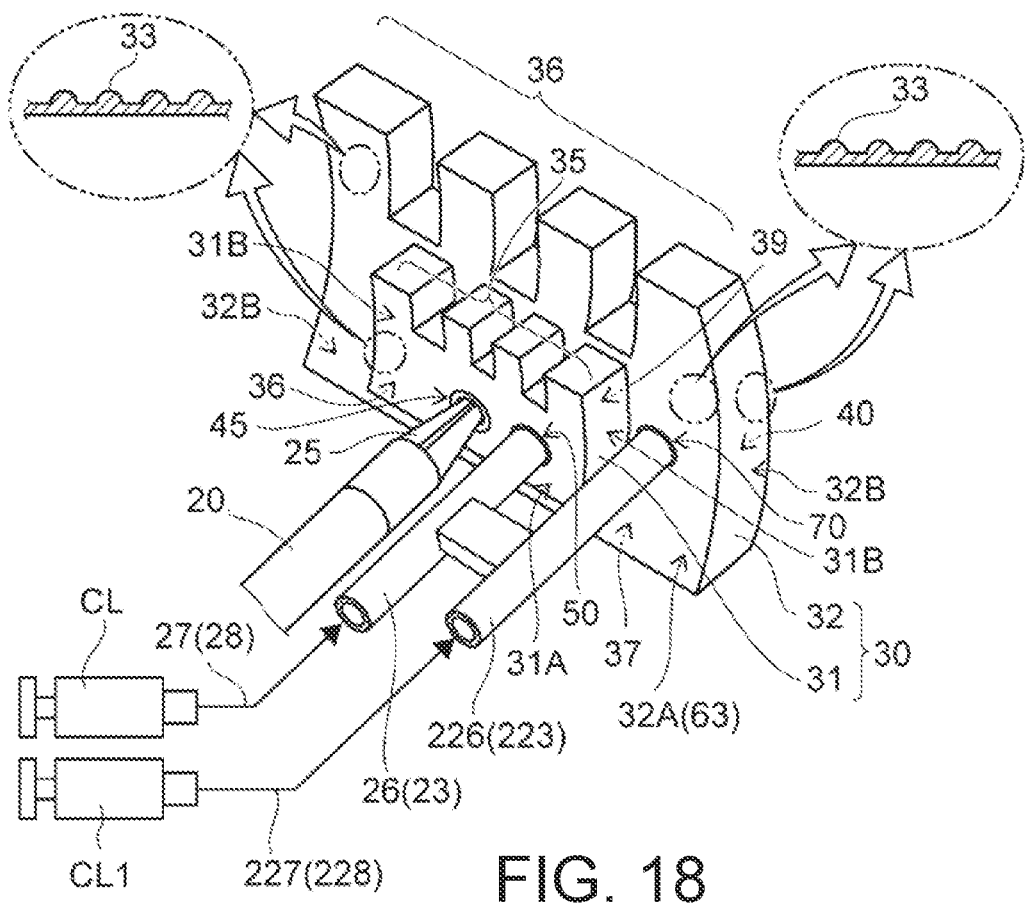
FIG. 18 is a schematic diagram illustrating an expandable body of the organ retraction device illustrated in FIG. 16 in a state where the expandable body is expanded to a predetermined size and shape in accordance with examples of the present disclosure.

As illustrated in FIGS. 17 and 18, the forceps 20 have been inserted through the first lumen 21. The first lumen 21 has an inner diameter of a size large enough to permit insertion of the grasp portion 25 of the forceps 20 and the expandable body 30 in the collapsed state therethrough.

The forceps 20 have the hand control part 24 and the grasp portion 25. When a healthcare practitioner manipulates the hand control part 24, the grasp portion 25 is operated open or closed. The expandable body 30 is grasped by the grasp portion 25, and the grasp portion 25 is detachably, liquid-tightly, and/or gas-tightly connected to the expandable body 30.

As illustrated in FIG. 17, the first catheter 23 and the second catheter 223 are, for example, plastic-made, flexible tubular members. The first catheter 23 is inserted in the second lumen 22. The second catheter 223 is inserted in the third lumen 230.

The first catheter 23 is detachably, liquid-tightly, and/or gas-tightly connected at the one end portion (e.g., inner end portion) 26 thereof to only the first expandable section 31 of the expandable body 30 in the abdominal cavity 1000. Similarly, the second catheter 223 is detachably, liquid-tightly, and/or gas-tightly connected at one end portion (e.g., inner end portion) 226 thereof to only the second expandable section 32 of the expandable body 30 in the abdominal cavity 1000.

The first catheter 23 has the connector portion 28 at the other end portion (e.g., outer end portion) 27 thereof. The connector portion 28 is connected to the fluid supplier CL such as a syringe. The fluid supplier CL supplies the fluid into only the first expandable section 31 of the expandable body 30 through the first catheter 23, whereby only the first expandable section 31 in the collapsed state is expanded, and is allowed to hold an expanded state.

On the other hand, the second catheter 223 has a connector portion 228 at the other end portion (e.g., outer end portion) 227 thereof. The connector portion 228 is connected to a fluid supplier CL1 such as a syringe. The fluid supplier CL1 supplies the fluid into only the second expandable section 32 of the expandable body 30 through the second catheter 223, whereby only the second expandable section 32 in the collapsed state is expanded, and is allowed to hold an expanded state. Examples of the fluid which the fluid suppliers CL and CL1 supply may include, but are in no way limited to, gases such as a carbon dioxide gas and air, and liquids such as physiological saline.

Referring to FIGS. 17 to 19C, the expandable body 30 will be described next.

Figure 19A:
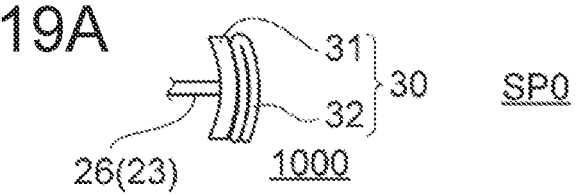
FIGS. 19A to 19C are views illustrating the expandable body of the organ retraction device illustrated in FIG. 16, in which the expandable body expands from a collapsed state to an expanded state as illustrated in FIG. 18.
Figure 19B:
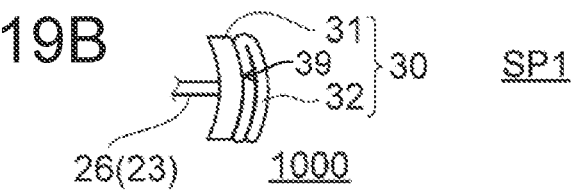
Figure 19C:
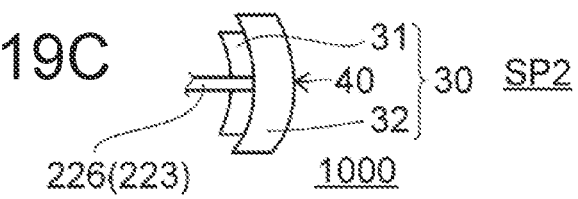

FIG. 18 illustrates the expandable body 30 in an expanded state, and FIGS. 19A to 19C illustrates the expandable body 30 expanded from a collapsed state to the expanded state as illustrated in FIG. 18. FIG. 19A illustrates the collapsed state, in which the first expandable section 31 and second expandable section 32 of the expandable body 30 are in collapsed states before injection of the fluid (e.g., this state may be referred to herein as the "preliminary stage SP0"). FIG. 19B illustrates a state, in which only the first expandable section 31 is expanded to a predetermined size and shape by injection of the fluid and the second expandable section 32 is still in the collapsed state (e.g., this state may be referred to herein as the "first stage SP1"). Further, FIG. 19C illustrates a state, in which the first expandable section 31 and the second expandable section 32 have been both expanded to predetermined sizes and shapes, respectively, by injection of the fluid into the first expandable section 31 and the second expandable section 32 to predetermined pressures or predetermined amounts (e.g., this state may be referred to herein as the "second stage SP2").

The first expandable section 31 and the second expandable section 32 are integral together (e.g., integrally formed, etc.). By injecting a predetermined amount of the fluid into the collapsed first expandable section 31 through the first catheter 23 in the preliminary stage SP0 as illustrated in FIGS. 17 and 19A, whereby as illustrated in FIG. 19B, in the first stage SP1, only the first expandable section 31 is expanded to the predetermined size and shape, and the second expandable section 32 is allowed to still remain in the collapsed state. When, as illustrated in FIG. 19C, the fluid is further injected to the predetermined pressure or predetermined amount through the second catheter 223 in the second stage SP2, the second expandable section 32 is expanded to the predetermined size and shape.

The fluid supplier CL is configured such that, when a healthcare practitioner depresses the push part (e.g., plunger, etc.) of the fluid supplier CL (e.g., syringe, etc.) illustrated in FIG. 18, the predetermined amount of the fluid in the fluid supplier CL is supplied to a side of only the first expandable section 31 of the expandable body 30 through the connector portion 28 and the first catheter 23. Similarly, the fluid supplier CL1 is configured such that, when the healthcare practitioner depresses the push part (e.g., plunger, etc.) of the fluid supplier CL1 (e.g., syringe, etc.) illustrated in FIG. 18, the predetermined amount of the fluid in the fluid supplier CL1 is supplied to a side of only the second expandable section 32 of the expandable body 30 through the connector portion 228 and the second catheter 223.

Taking a laparoscopic surgery for bowel cancer as an example as illustrated in FIG. 19, the first expandable section 31 plays a role to push aside or retract the small intestine 1002 or the like, which lies over the large intestine 1001, and to expose the large intestine 1001 as the target organ for the surgery. On the other hand, the second expandable section 32 plays a role to fix the retracted small intestine 1002 or the like to avoid its dislocation, or movement from the pushed aside or retracted position, in the abdominal cavity 1000. The volume of the second expandable section 32 in the expanded state is set great compared with the volume of the first expandable section 31 in the state expanded to the predetermined size and shape.

In the first stage SP1 of FIG. 19B, the first expandable section 31 is expanded in the vicinity of the distal end opening 10 of the trocar tube T illustrated in FIGS. 16 and 17, but the second expandable section 32 has not been expanded and still remains collapsed. In this state, the pressing surface portion 39, which is formed as a convex surface, of the first expandable section 31 plays a role to push aside or retract the small intestine 1002 or the like that lies over the large intestine as the target organ for the surgery. In the state that the first expandable section 31 and the second expandable section 32 have been both expanded to the predetermined sizes and shapes in the second stage SP2 as illustrated in FIG. 19C, the pressing surface portion 40 then plays a role to fix the retracted other organ, for example, the small intestine 1002 or the like to avoid its dislocation in the abdominal cavity 1000.

As illustrated in FIG. 18, the first expandable section 31 has the connection port 45 and the fluid injection port 50 on the side of the attachment surface 31A. The grasp portion 25 of the forceps 20 is inserted in the connection port 45. In this state, the first expandable section 31 is detachably grasped by the grasp portion 25 of the forceps 20. The grasp portion 25 is liquid-tightly and/or gas-tightly connected to the connection port 45 in the abdominal cavity 1000, so that the fluid injected into the first expandable section 31 does not leak from the connection port 45. The one end portion 26 of the first catheter 23 is detachably, liquid-tightly, and/or gas-tightly connected to the fluid injection port 50 of the expandable body 30 in the abdominal cavity 1000. The fluid can therefore be injected to the predetermined pressure or predetermined amount in the first expandable section 31 through the one end portion 26 of the first catheter 23 without leakage at the fluid injection port 50.

As illustrated in FIG. 18, the second expandable section 32 has the fluid injection port 70 in the inner surface portion 32A (e.g., partition 63). The second catheter 223 is detachably, liquid-tightly, and/or gas-tightly connected at the one end portion 226 thereof to a fluid injection port 70 of the second expandable section 32 in the abdominal cavity 1000. The fluid injection port 50 serves as a first fluid injection port, while the fluid injection port 70 serves as a second fluid injection port. In the first stage SP1 illustrated in FIG. 19B, the fluid can therefore be injected into only the first expandable section 31 through the one end portion 26 of the first catheter 23 without leakage at the fluid injection port 50. Similarly, in the second stage SP2 illustrated in FIG. 19C, the fluid can be similarly injected to the predetermined pressure or predetermined amount in only the second expandable section 32 through the one end portion 226 of the second catheter 223 without leakage at the fluid injection port 70.

The first expandable section 31 and the second expandable section 32 illustrated in FIG. 18 may have, at the surfaces thereof, fine wave-shaped or concavo-convex shaped portions 33. An increased friction force is therefore provided between the first and second expandable sections 31 and 32 and the organ, so that the operation to push aside or retract and to fix the organ can be performed with ease. Accordingly, the expandable body 30 can reliably perform the pushing aside or retraction of the small intestine 1002 or the like to have the large intestine 1001 exposed as the target organ for the surgery, and also the fixation of the retracted small intestine 1002 or the like to avoid its dislocation, or movement, in the abdominal cavity 1000 (e.g., during surgery). In particular, at least the pressing surface portion 40 may be provided with the fine wave-shaped or concavo-convex shaped portion 33. This enables to more reliably fix the retracted small intestine 1002 or the like to avoid its dislocation in the abdominal cavity 1000.

Referring next to FIGS. 20A to 20C, structural examples of the connection port 45, the fluid injection port 50, and the fluid injection port 70 of the first expandable section 31 will be described. FIG. 20A illustrates an example structure of the connection port 45. FIG. 20B illustrates an example structure of the fluid injection port 50. FIG. 20C illustrates an example structure of the fluid injection port 70. The structure illustrated in FIG. 20A is the same as that illustrated and described in conjunction with FIG. 11A, and its description is omitted accordingly.

In the first stage SP1 of FIG. 20B, the fluid is injected to a predetermined pressure or predetermined amount in only the first expandable section 31 through the one end portion 26 of the first catheter 23. In the second stage SP2 of FIG. 20C, the fluid is injected to a predetermined pressure or predetermined amount in only the second expandable section 32 through the one end portion 226 of the second catheter 223.

In the first stage SP1 of FIG. 20B, the one end portion 26 of the first catheter 23 is detachably, liquid-tightly, and/or gas-tightly connected to the fluid injection port 50 in the attachment surface 31A of the first expandable section 31 in the abdominal cavity 1000. The first catheter 23 has the flange portion 26F at the one end portion 26 thereof. The flange portion 26F is fixed by the fixing member 31H on the inner surface on the side opposite to the attachment surface 31A. The flange portion 26F does not come off in the direction X from the fluid injection port 50. In a case of detaching the flange portion 26F from the attachment surface 31A, however, it is only necessary to simply pull out the one end portion 26 of the first catheter 23 in the direction X1. As a result, the flange portion 26F is forcedly pulled out of the fluid injection port 50.

As illustrated in FIG. 20B, the check valve 60 is disposed on the fixing member 31H. The check valve 60 has fluid flow openings 61 and the spherical valve element 62. The spherical valve element 62 (e.g., ball, etc.) is movable in the direction X within the check valve 60. When the fluid flows from the one end portion 26 of the first catheter 23 into the check valve 60 as indicated by the arrow E, the fluid is injected into the first expandable section 31 by way of the fluid flow openings 61. The first expandable section 31 is therefore expanded to a predetermined size and shape as illustrated in FIGS. 19A to 19B. When the supply of the fluid is stopped, the spherical valve element 62 moves leftward by the pressure of the fluid in the first expandable section 31, and closes up the fluid flow openings 61. When, as described above, the injection of the fluid is stopped and the first expandable section 31 is expanded to the predetermined size and shape, the spherical valve element 62 moves leftward (e.g., in the direction X1) and closes up the fluid flow openings 61 so that the expanded state of the first expandable section 31 is maintained.

In the second stage SP2 of FIG. 20C, the one end portion 226 of the second catheter 223 is detachably, liquid-tightly, and/or gas-tightly connected to the fluid injection port 70 in the attachment surface 32A of the second expandable section 32 in the abdominal cavity 1000. The second catheter 223 has a flange portion 226F at the one end portion 226 thereof. The flange portion 226F is fixed by a fixing member 32H on an inner surface on the side opposite to the attachment surface 32A. The flange portion 226F does not come off in the direction X from the fluid injection port 70. In a case of detaching the flange portion 226F from the attachment surface 32A, however, it is only necessary to simply pull out the one end portion 226 of the second catheter 223 in the direction X1. As a result, the flange portion 226 is forcedly pulled out of the fluid injection port 70.

As illustrated in FIG. 20C, a check valve 260 is disposed on the fixing member 32H. The check valve 260 has fluid flow openings 261 and the spherical valve element 262. The spherical valve element 262 is movable in the direction X within the check valve 260. When the fluid flows from the one end portion 226 of the second catheter 223 into the check valve 260 as indicated by the arrow E, the fluid is injected into the second expandable section 32 by way of the fluid flow openings 261. The second expandable section 32 is therefore expanded to a predetermined size and shape. When the supply of the fluid is stopped, the spherical valve element 262 is pushed in the direction X1 by the pressure of the fluid in the second expandable section 32, and closes up the fluid flow openings 261. Therefore, the fluid does not leak out from the second expandable section 32, and the expanded state of the second expandable section 32 in the predetermined size and shape is maintained.

Using an example in which the above-mentioned organ retraction device 101 is applied to a laparoscopic surgery for bowel cancer, a method of use of the organ retraction device 101 will be described next.

As illustrated in FIGS. 16 and 17, the expandable body 30 is collapsed small, and is grasped by the grasp portion 25 of the forceps 20. As illustrated in FIG. 16, the trocar tube T is inserted into the incision site H, and the forceps 20 and the expandable body 30 of the organ retraction device 101 are inserted into the abdominal cavity 1000 through the trocar tube T.

When a pushing-aside operation is performed with the expandable body 30 in retraction, the large intestine 1001 as the target organ for the surgery is exposed by pushing aside the small intestine 1002 or the like. When the fluid flows into the check valve 60 from the one end portion 26 of the first catheter 23 as indicated by the arrow E illustrated in FIG. 20B, the fluid is injected into the first expandable section 31 by way of the fluid flow openings 61.

Figure 21A:
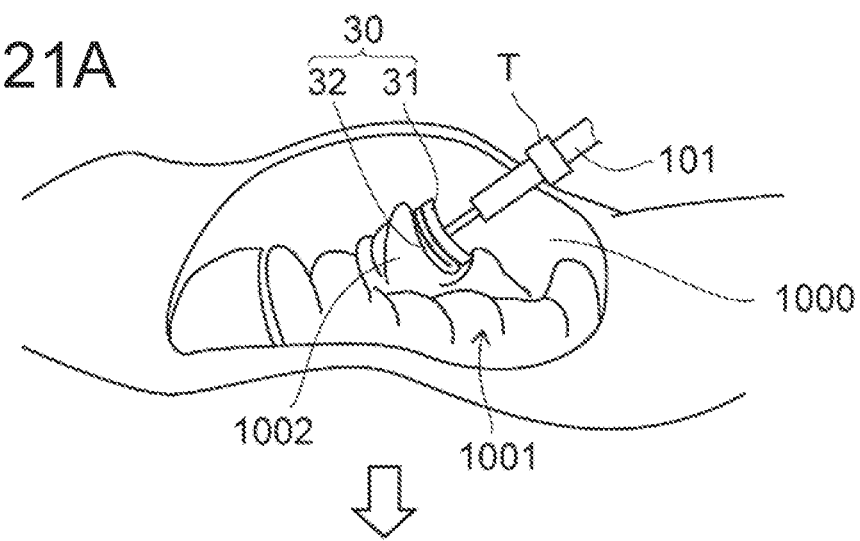
FIGS. 21A to 21C are views illustrating a pushing aside or retracting operation of an organ, a fixing operation of the organ, and a manner of detaching a pair of forceps from the expandable body when the expandable body is placed in the abdominal cavity, respectively, all, using the organ retraction device illustrated in FIG. 16.

As illustrated from FIG. 19A to FIG. 19B, the first expandable section 31 is expanded to the predetermined size and shape. When the healthcare practitioner manipulates the hand control part 24 of FIG. 16 with only the first expandable section 31 of the expandable body 30 expanded, the first expandable section 31 pushes aside the small intestine 1002 or the like in the abdominal cavity 1000 as illustrated by way of example in FIG. 21A. The first expandable section 31 is then placed at a predetermine site in the abdominal cavity 1000 by operation of the grasp portion 25 of the forceps 20. The large intestine 1001 as the target organ for the surgery is therefore exposed in the field of vision.

Figure 21B:
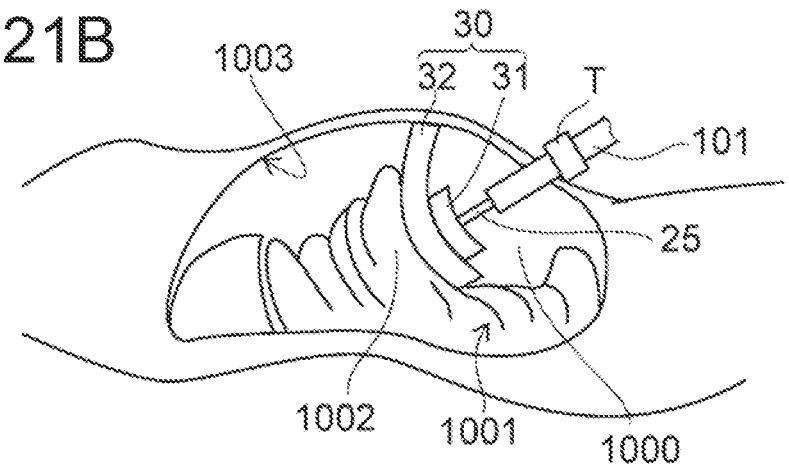

Next, the retracted small intestine 1002 or the like is fixed to avoid its dislocation. The state in which the large intestine 1001 as the target organ for the surgery is exposed in the field of vision is maintained accordingly. If the fluid now flows further into the check valve 260 from the one end portion 226 of the second catheter 223 as indicated by the arrow E in FIG. 20C, the fluid is injected into only the second expandable section 32 by way of the fluid flow openings 261. Therefore, the second expandable section 32 is expanded to the predetermined size or shape. FIG. 21B illustrates a state in which the small intestine 1002 or the like is fixed by the second expandable section 32. As illustrated in FIG. 18, the first expandable section 31 and the second expandable section 32 have the fine wave-shaped or concavo-convex shaped portions 33. When pushing aside or retracting and fixing the small intestine 1002 or the like, the first expandable section 31 and the second expandable section 32 can therefore produce friction to avoid slipping of the small intestine 1002 or the like, thereby enabling to reliably perform the retraction.

After the fixation of the small intestine 1002 or the like by the second expandable section 32, the expandable body 30, while being kept expanded, is placed in the abdominal cavity 1000 to maintain the small intestine 1002 or the like in the fixed state. As illustrated by way of example in FIG. 21C, a grasp portion 3 of the additional forceps 2 now grasps the grasp portion 25 of the forceps 20 in the abdominal cavity 1000. The forceps 20 are then pulled out in the direction X1, so that the grasp portion 25 of the forceps 20, the grasp portion 25 closing up the connection port 45, is detached from the connection port 45.

As a consequence, the grasp portion 25 of the forceps 20 is detached from the first expandable section 31, whereby the expandable body 30 (e.g., "a balloon," etc.) is placed in the abdominal cavity 1000. The placed expandable body 30 has the fine wave-shaped or concavo-convex shaped portions 33, and therefore can be fixed by friction relative to the abdominal wall 1003 and the organ. Furthermore, the expandable body 30 itself is firmly squeezed at upper and lower parts thereof by the abdominal wall 1003 and the organ, and therefore the expandable body 30 does not move.

It is to be noted that the forceps 20 detached from the expandable body 30 have the grasp portion 25, and the grasp portion 25 can be used in a similar manner as general forceps in surgery.

To recover the expandable body 30 in the expanded state from the abdominal cavity 1000, the size of the expandable body 30 needs to be made smaller by releasing the fluid such as a carbon dioxide gas or air from the first expandable section 31 and second expandable section 32 of the expandable body 30.

Figure 22A:
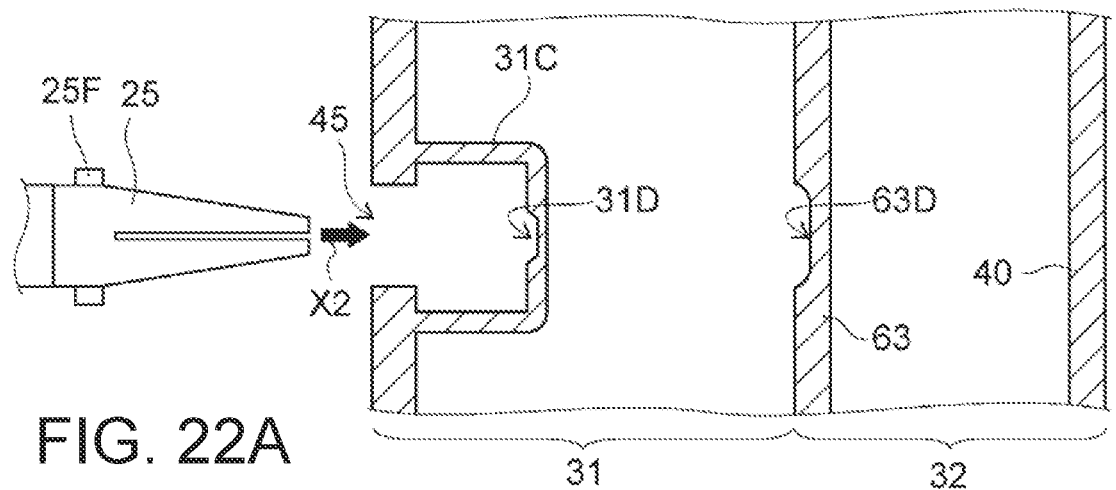
FIGS. 22A to 22C are schematic diagrams illustrating an example of a manner of releasing a fluid such as air from the expanded expandable body to cause contraction of the expandable body illustrated in FIG. 18.
Figure 22B:
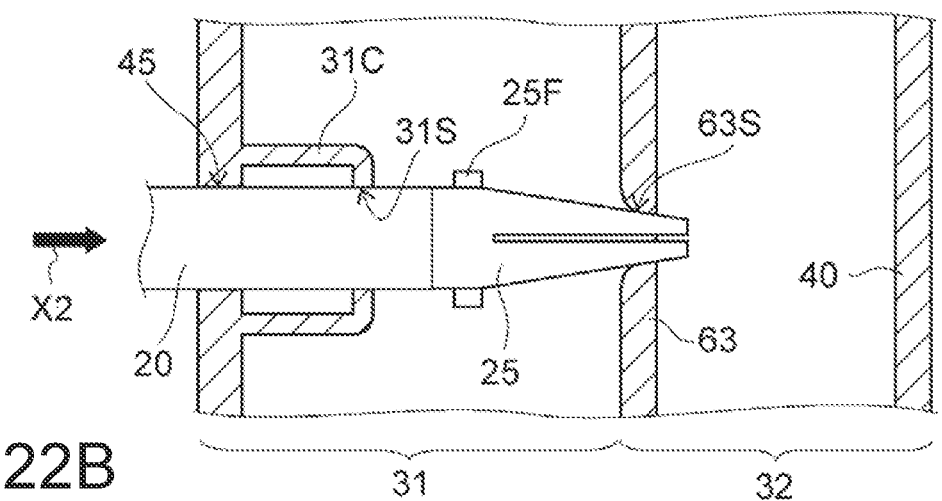
Figure 22C:
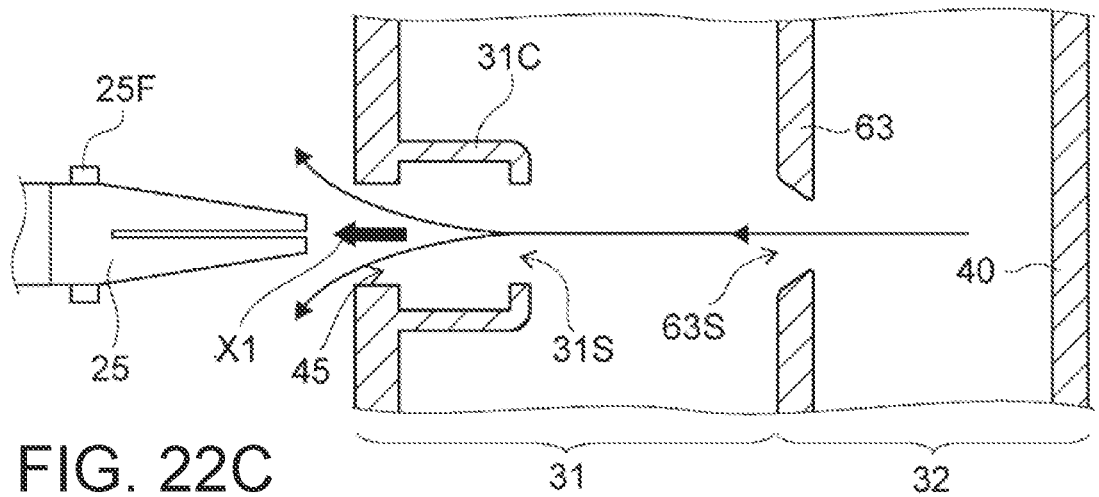

An example in which the fluid such as a carbon dioxide gas or air is released from the expandable body 30 is illustrated in FIGS. 22A to 22C. FIG. 22A illustrates a state in which the first expandable section 31 and the second expandable section 32 have been expanded to the predetermined sizes and shapes, respectively. In FIG. 22B, by manipulating the hand control part 24 illustrated in FIG. 7, the grasp portion 25 of the forceps 20 is inserted deep under pressure in the direction X2 through the connection port 45. Therefore, the grasp portion 25 breaks through the thin wall portion 31D to form the hole 31S, and also breaks through the thin wall portion 63D of the partition 63 to form the hole 63S.

As illustrated in FIG. 22C, the grasp portion 25 of the forceps 20 is then pulled out in the direction X1. As a consequence, the fluid in the first expandable section 31 and the fluid in the second expandable section 32 are released from the first expandable section 31 and the second expandable section 32 by way of the hole 31S, the hole 63S, and the connection port 45. Accordingly, the expandable body 30 itself undergoes elastic contraction, and is allowed to compact and collapse, as illustrated in FIGS. 23A, 23B, and 23C.

Figure 21C:
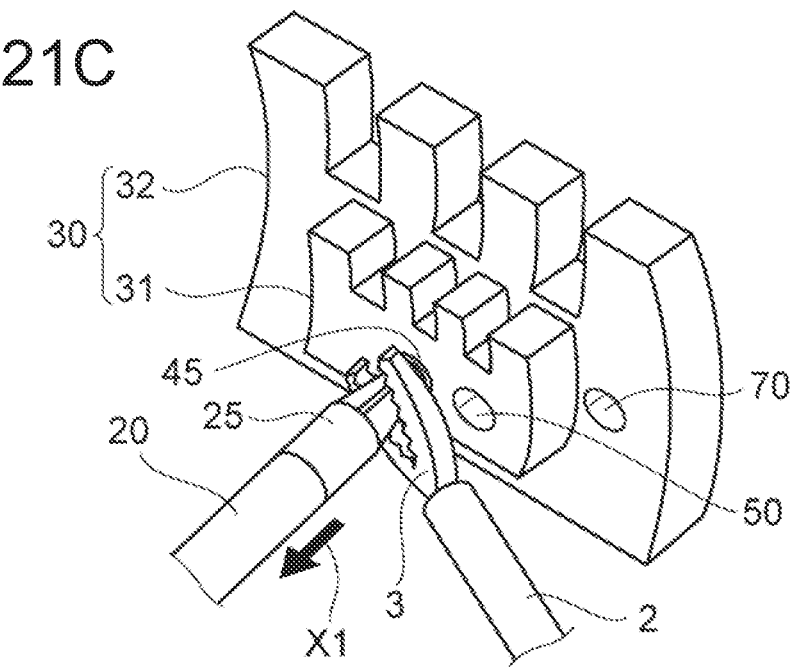
Figure 23A:
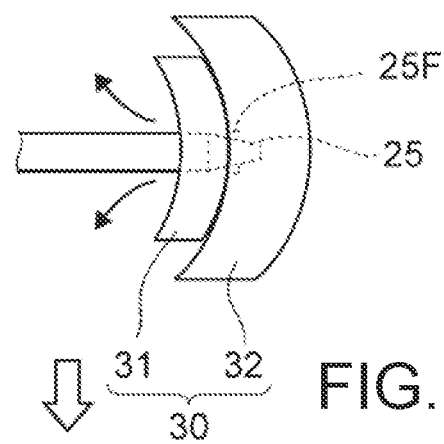
FIGS. 23A to 23D are schematic diagrams illustrating a manner of releasing the fluid, such as air, from the expanded expandable body and causing contraction of the expandable body as illustrated in FIGS. 22A to 22C, and recovering the contracted expandable body from the interior of the abdominal cavity in accordance with examples of the present disclosure.
Figure 23B:
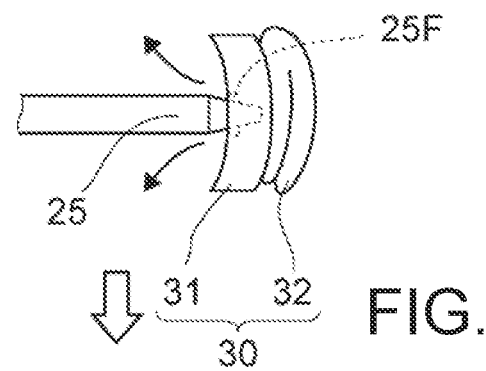
Figure 23C:
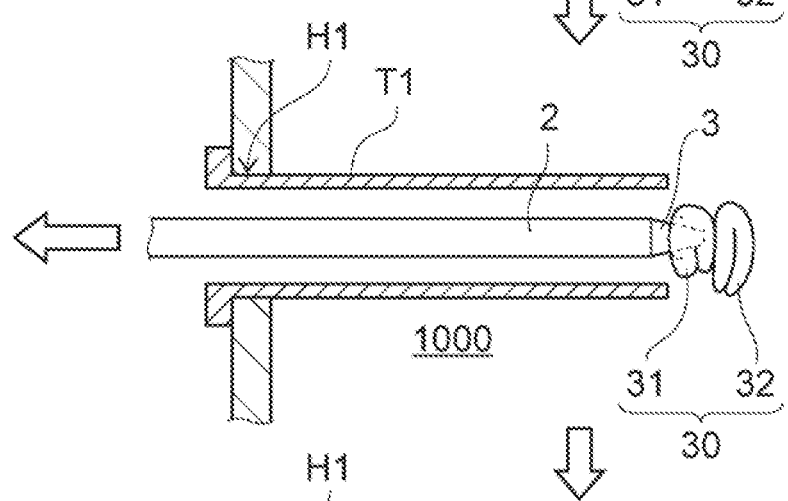
Figure 23D:
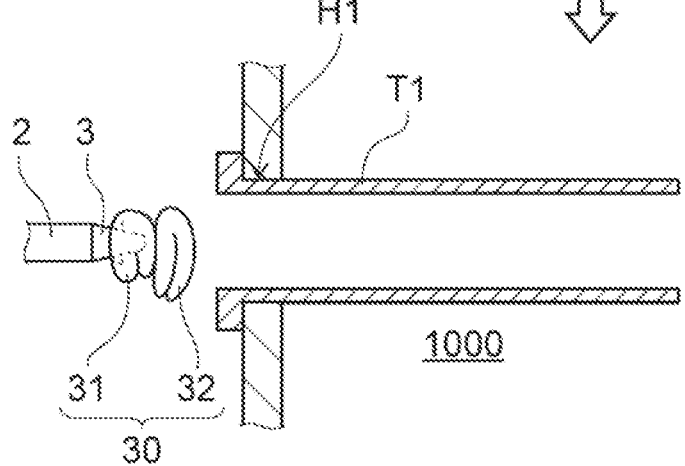

After that, the compacted expandable body 30 can be recovered by grasping it, for example, with the grasp portion 25 of the forceps 20 illustrated in FIGS. 7, 23A, and 23B, and taking it out of the body from the abdominal cavity 1000 through the trocar tube T. As an alternative, the compacted expandable body 30 can also be recovered as illustrated in FIGS. 23C and 23D by grasping it with the grasp portion 3 of the additional forceps 2, which are illustrated in FIG. 21C, instead of the grasp portion 25 of the forceps 20 and taking it out of the body from the abdominal cavity 1000.

When a carbon dioxide gas is used as the fluid, the expandable body 30 may be taken out using the grasp portion 25 of the forceps 20 after causing contraction of the expandable body 30 by cutting the expandable body 30 at an appropriate part thereof with the grasp portion 25 and discharging a carbon dioxide gas from the expandable body 30 into the abdominal cavity 1000.

The use of the above-described organ retraction device of each example or embodiment of the present disclosure enables to safely and reliably perform the pushing aside or retraction of another organ, which lies over a target organ for a surgery, to expose the target organ for a surgery, and the fixation of the retracted other organ in position. Specifically, the organ retraction device of each example or embodiment of the present disclosure has several merits as will be described next.

In the first-stage expanding operation, the expandable body pushes aside or retracts another organ that lies over a target organ for a surgery, for example, another organ that lies over the large intestine in a surgery for bowel cancer, for example, the small intestine or the like to keep the large intestine exposed as the target organ for the surgery. In the second-stage expanding operation, the expandable body then fixes the retracted another body, for example, the small intestine or the like to avoid its dislocation, or movement from the retracted position, in the abdominal cavity.

Since a strong fixing force can be produced for an organ as described above, it is no longer necessary to apply acute head-down tilt for a long time. The risk associated with head-down tilt can be reduced accordingly. Patients who have heretofore been unable to have a surgery due to a potential danger of head-down positioning (for example, patients who are at a high risk of elevated intraocular pressure) can now have the surgery, leading to an expansion of patients to be subjected to a surgery. Moreover, for patients who have needed a risk prevention (for example, administration of heparin, wearing of elastic compression stockings, or the like for high DVT risk patients), these preventive measures are considered to be unnecessary so that medical economic effects are expected.

In a surgery of bowel cancer with the organ retraction device of each embodiment of the present disclosure, the surgery time can be shortened, for example, by 50 minutes compared with the conventional manner. Owing to this reduction of time, the time required for a laparoscopic surgery is shortened to a similar time as in a conventional open abdominal surgery.

The performance of pushing aside or retraction operation of the organ by the first expandable section enables gentle handling of the organ in the first stage SP1, so that the injury risk of the organ can be decreased. Further, the second expandable section performs the fixation of the retracted organ, thereby enabling to secure a sufficient field of vision in the abdominal cavity. Accordingly, the possibility of a mistake during operation of a pair of forceps or an electric scalpel is decreased, the injury risk of the organ can be reduced, and the pushing aside or retraction operation of the organ can be reliably performed with assurance of safety. The use of the organ retraction device of each example or embodiment of the present disclosure can lighten the surgeon's load in a laparoscopic surgery.

In each example or embodiment, the first expandable section and second expandable section of the expandable body can be expanded by delivering a fluid from the grasp portion of the forceps as a surgical instrument into the expandable body. When the grasp portion of the forceps is detached from the expandable body, the grasp portion can perform grasping operation as a function of the forceps. The forceps can therefore be used according to the procedure or operative technique in the surgery.

The examples or embodiments of the present disclosure have been described above. However, the present disclosure should not be limited to the above-described examples or embodiments, and various modifications can be made within a scope not departing from the claims. The configurations of the above-described examples or embodiments can be omitted in part, or can be combined as desired in ways different from the above-described examples or embodiments.

The organ retraction devices of the examples or embodiments of the present disclosure are used for operative techniques of a laparoscopic surgery, but can also be used in different types of surgeries. The first expandable section and the second expandable section have the curved shapes, respectively, but may be planar. In addition to bowel cancer, the organ retraction devices of the examples or embodiments of the present disclosure can be also used for a surgery of other diseased parts such as rectal cancer.

What is claimed is:

1. An organ retraction device comprising:
   a surgical instrument; and an expandable body operable for expansion by connection of the surgical instrument thereto, wherein
the expandable body includes:
- a first expandable section configured to be expandable to a first predetermined size and shape in a first stage to move an organ in an abdominal cavity, and
- a second expandable section configured to be expandable to a second predetermined size and shape in a second stage to fix the organ, wherein the surgical instrument includes a pair of forceps having a grasp portion, and delivers a fluid with the grasp portion connected to the expandable body so that the first expandable section and the second expandable section are expanded in the abdominal cavity, and wherein the grasp portion is configured to be capable of grasping when the surgical instrument is detached from the expandable body.

2. The organ retraction device according to claim 1, wherein the first expandable section and the second expandable section have collapsed conformations, respectively, before expansion.

3. The organ retraction device according to claim 1, wherein the expandable body is sealed so that a fluid supplied from a side of the surgical instrument, to which the expandable body is connected, into the expandable body is prevented from leaking out of the expandable body.

4. The organ retraction device according to claim 1, wherein the expandable body is made of a pliable material.

5. The organ retraction device according to claim 1, wherein the expandable body has a hand shape.

6. The organ retraction device according to claim 1, wherein the expandable body has a C shape.

7. The organ retraction device according to claim 1, wherein the expandable body has a wavy surface.

8. The organ retraction device according to claim 1, wherein the expandable body includes a magnet and is fixable to the surgical instrument by the magnet.

9. The organ retraction device according to claim 1, wherein the expandable body is made of a bioabsorbable material.

10. The organ retraction device according to claim 1, wherein the expandable body has a size selected according to a size of the abdominal cavity.

11. The organ retraction device according to claim 1, wherein the expandable body is produced by a three-dimensional printer.

12. The organ retraction device according to claim 1, wherein a material having radiopacity is used in the expandable body.

13. The organ retraction device according to claim 1, wherein the surgical instrument includes an electric scalpel, and the expandable body has an insulating coating so that the expandable body does not puncture even if the electric scalpel comes into contact with the expandable body.

14. The organ retraction device according to claim 1, wherein a water-absorbing material is used in a part of the expandable body, where the expandable body comes into contact with an abdominal wall.

15. An organ retraction device comprising:
- a surgical instrument; and
- an expandable body operable for expansion by connection of the surgical instrument thereto, wherein
the expandable body includes:
- a first expandable section configured to be expandable to a first predetermined size and shape in a first stage to move an organ in an abdominal cavity, and
- a second expandable section configured to be expandable to a second predetermined size and shape in a second stage to fix the organ; and
- a valve structure configured to suppress leakage of a fluid in the expandable body to an outside of the expandable body when the surgical instrument is detached from the expandable body, wherein, after expansion, the expandable body contracts when the surgical instrument detached from the expandable body is inserted into the valve structure.

16. The organ retraction device according to claim 15, wherein the surgical instrument is configured to be connected to the expandable body when pierced into the valve structure.

17. The organ retraction device according to claim 15, wherein the surgical instrument is configured to be connected to the expandable body when rotated relative to the valve structure.

18. An organ retraction device comprising:
- a surgical instrument; and
- an expandable body operable for expansion by connection of the surgical instrument thereto, wherein the expandable body comprises:
- a first expandable section configured to be expandable to a first predetermined size and shape in a first stage to move an organ in an abdominal cavity, and
- a second expandable section configured to be expandable to a second predetermined size and shape in a second stage to fix the organ, wherein the expandable body is configured to contract when, after expansion, the surgical instrument detached from the expandable body cuts the expandable body.

* * * * *